(12) United States Patent
Zheng et al.

(10) Patent No.: US 8,927,121 B2
(45) Date of Patent: Jan. 6, 2015

(54) EMISSIVE ARYL-HETEROARYL COMPOUNDS

(71) Applicant: Nitto Denko Corporation, Osaka (JP)

(72) Inventors: Shijun Zheng, San Diego, CA (US); Jensen Cayas, Bonita, CA (US); Sheng Li, Vista, CA (US); Amane Mochizuki, Carlsbad, CA (US); Hyun Sik Chae, San Diego, CA (US); Brett T. Harding, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/925,625

(22) Filed: Jun. 24, 2013

(65) Prior Publication Data

US 2013/0284907 A1 Oct. 31, 2013

Related U.S. Application Data

(63) Continuation of application No. 12/825,953, filed on Jun. 29, 2010, now abandoned.

(60) Provisional application No. 61/221,472, filed on Jun. 29, 2009.

(51) Int. Cl.
*H01L 51/54* (2006.01)
*H01L 51/00* (2006.01)
(Continued)

(52) U.S. Cl.
CPC ............ *H01L 51/006* (2013.01); *C07D 235/18* (2013.01); *C07D 263/57* (2013.01); *C07D 277/66* (2013.01); *C07D 403/12* (2013.01); *C07D 413/10* (2013.01); *C09K 11/06* (2013.01); *H05B 33/14* (2013.01); *G01J 1/42* (2013.01); *H01L 51/0071* (2013.01); *H01L 51/0072* (2013.01); *H05B 37/00* (2013.01); *C09K 2211/1007* (2013.01); *C09K 2211/1011* (2013.01); *C09K 2211/1033* (2013.01); *C09K 2211/1037* (2013.01); *C09K 2211/1044* (2013.01); *Y10S 428/917* (2013.01)
USPC ........... 428/690; 428/917; 313/504; 313/505; 313/506; 257/40; 257/E51.05; 257/E51.026; 257/E51.032; 548/304.1; 548/418; 548/440; 546/79; 546/81; 546/101; 544/234

(58) Field of Classification Search
USPC .................. 428/690, 917; 313/504, 505, 506; 257/40, E51.05, E51.026, E51.032; 548/304.1, 418, 440; 546/79, 81, 101; 544/234
See application file for complete search history.

(56) References Cited

U.S. PATENT DOCUMENTS

| | | |
|---|---|---|
| 3,957,666 A | 5/1976 | Hammann et al. |
| 5,417,885 A | 5/1995 | Suzuki et al. |

(Continued)

FOREIGN PATENT DOCUMENTS

| | | |
|---|---|---|
| DE | 4301700 | 7/1994 |
| EP | 0 499 222 A1 | 8/1992 |

(Continued)

OTHER PUBLICATIONS

Billmeyer, et al., "Principles of Color Technology", 2nd edition, John Wiley & Sons, Inc., New York, 1981.

(Continued)

*Primary Examiner* — Gregory Clark
(74) *Attorney, Agent, or Firm* — Knobbe, Martens, Olson & Bear LLP

(57) ABSTRACT

Disclosed herein are compounds represented by Formula 1, wherein $R^1$, $Ar^1$, X, $Ar^2$, $Ar^3$, and Het are described herein. Compositions and light-emitting devices related thereto are also disclosed.

18 Claims, 4 Drawing Sheets

(51) Int. Cl.

| | |
|---|---|
| *C07D 235/18* | (2006.01) |
| *C07D 263/57* | (2006.01) |
| *C07D 277/66* | (2006.01) |
| *C07D 403/12* | (2006.01) |
| *C07D 413/10* | (2006.01) |
| *C09K 11/06* | (2006.01) |
| *H05B 33/14* | (2006.01) |
| *G01J 1/42* | (2006.01) |
| *H05B 37/00* | (2006.01) |

(56) References Cited

U.S. PATENT DOCUMENTS

| | | | |
|---|---|---|---|
| 6,232,322 | B1 | 5/2001 | Malamas et al. |
| 6,359,107 | B1 | 3/2002 | Connell et al. |
| 6,596,350 | B2 | 7/2003 | Tarumi et al. |
| 6,905,741 | B2 | 6/2005 | Manabe et al. |
| 7,314,693 | B2 | 1/2008 | Ikegami et al. |
| 7,373,060 | B2 | 5/2008 | Satake et al. |
| 7,851,074 | B2 | 12/2010 | Kido et al. |
| 8,323,805 | B2 | 12/2012 | Zheng et al. |
| 8,354,668 | B2 | 1/2013 | Zheng |
| 8,420,235 | B2 | 4/2013 | Zheng |
| 2007/0122654 | A1 | 5/2007 | Lai et al. |
| 2008/0064662 | A1 | 3/2008 | Saha et al. |
| 2009/0008163 | A1 | 1/2009 | Chikazawa et al. |
| 2009/0134783 | A1* | 5/2009 | Lin et al. ............ 313/504 |
| 2010/0060154 | A1 | 3/2010 | Nomura et al. |
| 2010/0308310 | A1 | 12/2010 | Zheng et al. |
| 2010/0308716 | A1 | 12/2010 | Zheng |
| 2010/0326526 | A1 | 12/2010 | Zheng |
| 2010/0327269 | A1 | 12/2010 | Zheng |

FOREIGN PATENT DOCUMENTS

| | | | |
|---|---|---|---|
| EP | 0637624 | | 2/1995 |
| GB | 1 469 818 | A | 4/1977 |
| JP | 64-009959 | | 1/1989 |
| JP | 04-225365 | | 8/1992 |
| JP | 05-066593 | | 3/1993 |
| JP | 07-076542 | | 3/1995 |
| JP | 7-076542 | A | 3/1995 |
| JP | 7138568 | | 5/1995 |
| JP | 7207169 | | 8/1995 |
| JP | 10-340786 | A | 12/1998 |
| JP | 2002-025779 | | 1/2002 |
| JP | 2002-096558 | A | 4/2002 |
| JP | 2004-083513 | | 3/2004 |
| JP | 2005-255531 | | 9/2005 |
| JP | 2005-531618 | | 10/2005 |
| JP | 2006-273791 | | 10/2006 |
| JP | 2007-269772 | * | 10/2007 ........... C07D 235/18 |
| JP | 2008-536320 | | 9/2008 |
| JP | 2011-16798 | | 1/2011 |
| KR | 959189 | B1 | 5/2010 |
| TW | 200922926 | A | 6/2009 |
| WO | WO 99/58518 | A2 | 11/1999 |
| WO | WO 2004010996 | | 2/2004 |
| WO | WO 2006/100896 | | 9/2006 |
| WO | WO 2009/081873 | | 7/2009 |
| WO | WO 2010/141754 | | 12/2010 |
| WO | WO 2010/141758 | | 12/2010 |
| WO | WO 2011/008560 | | 1/2011 |

OTHER PUBLICATIONS

CIE 1971, International Commission on Illumination, Colorimetry: Official Recommendations of the International Commission on Illumination, Publication CIE No. 15 (E-1.3.1) 1971, Bureau Central de la CIE, Paris, 1971.

Gustafsson et al. "Flexible Light-Emitting Diodes Made from Soluble Conducting Polymer," Nature, Jun. 11, 1992, vol. 357, pp. 477-479.

International Search Report for Application No. PCT/US2010/040467, dated Nov. 25, 2010.

Kauffman, et al., Synthesis and Photophysical Properties of Fluorescent 2-aryl-1, 3-dialkylbenzimidazolium Ions and a 1-Alkyl-2-arylbenzimidazole with Excited State Intramolecular Proton-Transfer, J. Heterocyclic Chem., 31, pp. 957-965, Jul.-Aug. 1994.

Ge, et al., Spin-Coated Highly Efficient Phosphorescent Organic Light-Emitting Diodes Based on Bipolar Triphenylamine-Benzimidazole Derivatives, Advanced Functional Materials, 2008, pp. 584-590.

Ge, et al., Solution-Processible Bipolar Triphenylamine-Benzimidazole Derivatives for Highly Efficient Single-Layer Organic Light-Emitting Diodes, American Chemical Society, vol. 20, No. 7, 2008, pp. 2532-2537.

CAS Registry No. 168216-32-8 in 1 page, accessed Apr. 23, 2010.

Kim, et al., Synthesis and properties of highly fluorescent liquid crystals containing bexzoxazole moeity, Gordon and Breach Publishers, No. 337, 1999, pp. 405-408.

Malamas, et al., Novel Benzofuran and Benzothiophene Biphenyls as Inhibitors of Protein Tyrosine Phosphatase 1B with Antihyperglycemic Properties. Journal of Medicinal Chemistry (2000), 43(7), 1293-1310.

Results of Mar. 30, 2009 search of SureChem-patent_centric database.

Ribierre, Jean-Charles, et al., Effects of Viscoelastic Properties on the Dielectric and Electrooptic Responses of Low-Tg Guest-Host Polymers, Macromolecules 2003, vol. 36, pp. 2516-2525.

Ueda, et al., Synthesis of poly(benzothiazole)s by direct polycondensation of dicarboxylic acids with 2,5-diamino-1, 4-benzenedithiol dihydrochloride using phosphorus pentoxide/methaneusulfonic acid as condensing agent and solvent, Polymer Journal vol. 18, No. 2, 1986 pp. 117-122.

Vinodkumar, et al., Synthesis of highly functionalized 2-(substituted biphenyl)benzimidazoles via Suzuki-Miyaura cross-coupling reaction. Journal of Heterocyclic Chemistry (2007), 44(6), 1521-1523.

Miller et al., "Reactions of Polyfluoroarenes with Hexamethyldisilazane and with 1,1,1-Trimethyl-N,N-bis(trimethlsilyl) Stannaneamine in the Presence of Caesium Fluoride," Journal of Fluorine Chemistry, 1995, vol. 75, pp. 169-172.

Vlasov et al., "Kinetics of the Reaction of Aryl- and Diarylamine N-anions with p-nitrofluorobenzene in Dimethyl Sulfoxide," Zhurnal Organicheskoi Khimii, 1994, vol. 30, No. 10, pp. 1507-1512.

* cited by examiner

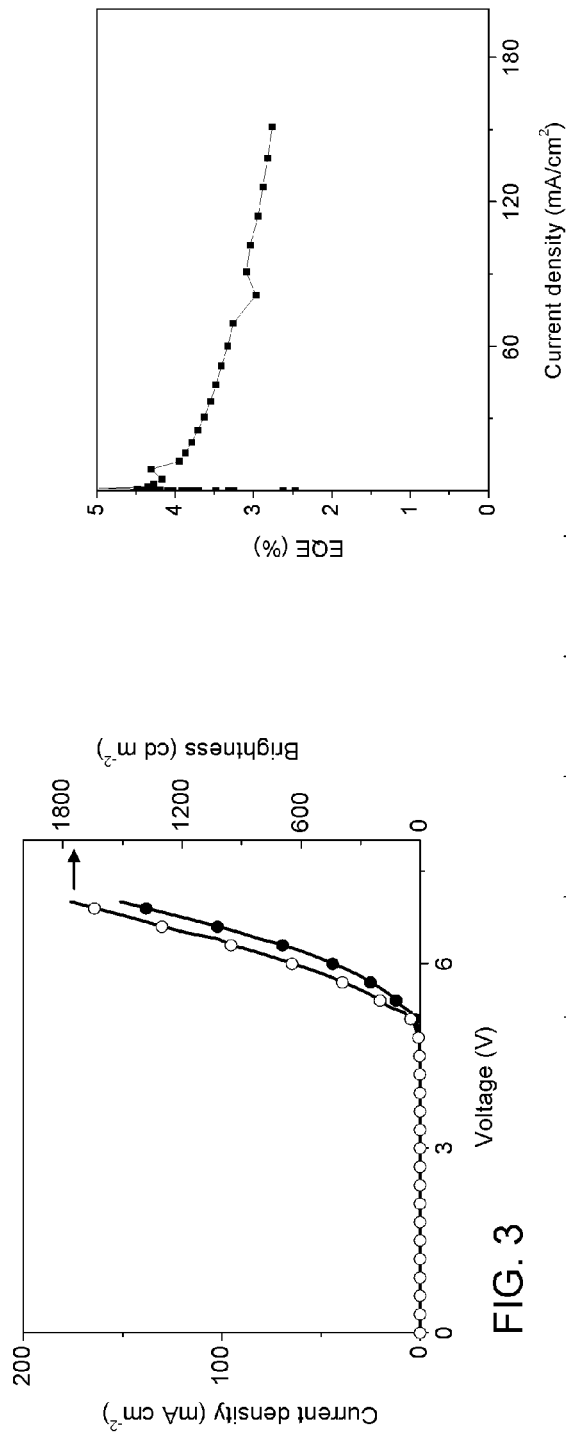
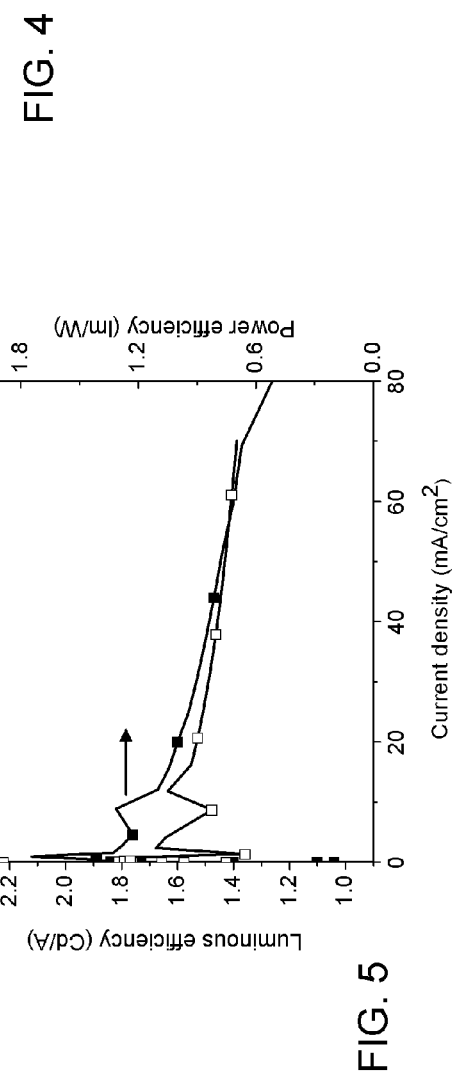
FIG. 3
FIG. 4
FIG. 5

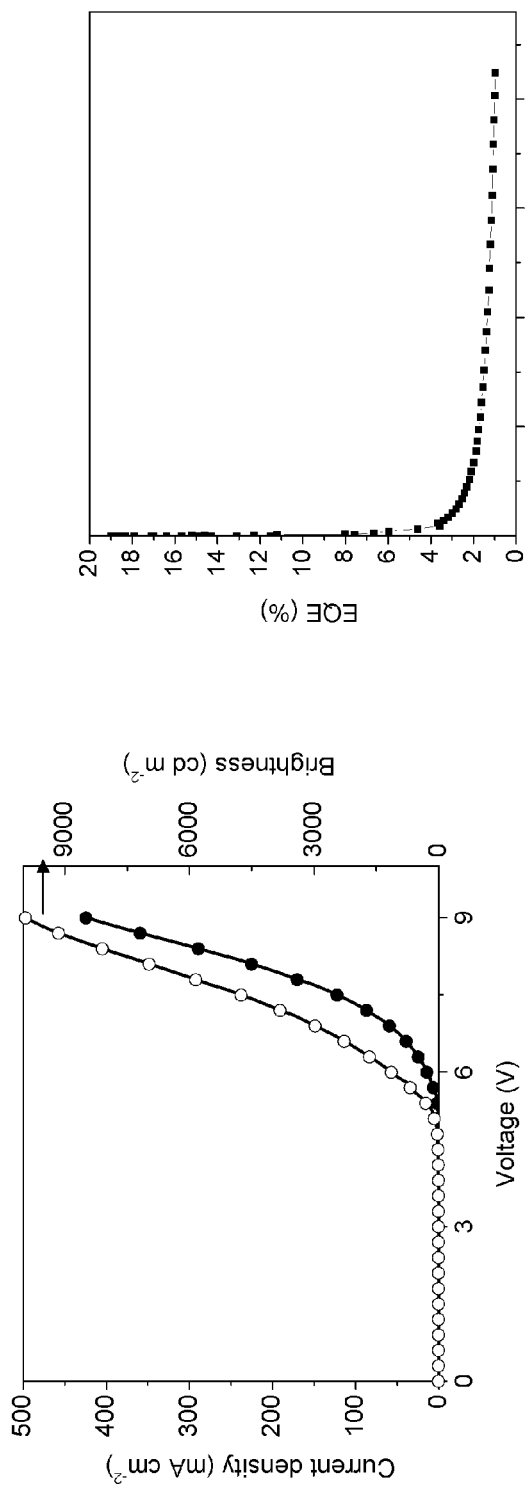
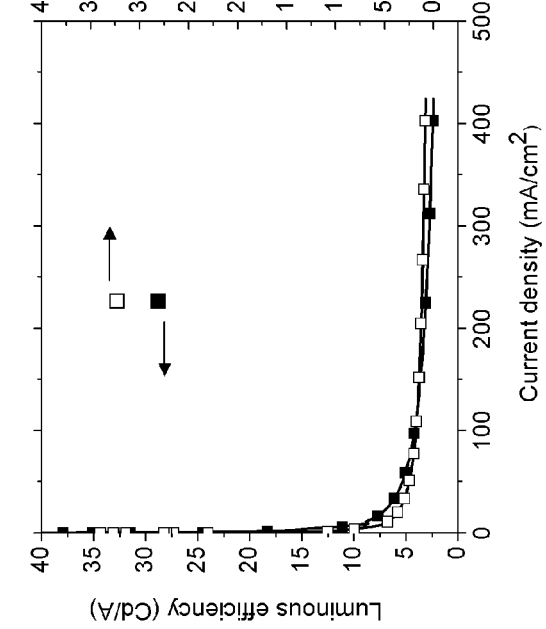
FIG. 8
FIG. 9
FIG. 10

EMISSIVE ARYL-HETEROARYL COMPOUNDS

CROSS-REFERENCE TO RELATED APPLICATIONS

This application is a continuation of U.S. patent application Ser. No. 12/825,953 filed Jun. 29, 2010, which claims the benefit of priority to U.S. Provisional Application No. 61/221,472, filed Jun. 29, 2009. These applications are hereby incorporated by reference in their entireties.

BACKGROUND

1. Field of the Invention

This invention relates to light-emitting compounds and compositions, as well as light-emitting devices that include the light-emitting compounds or compositions.

2. Description of the Related Art

Organic light-emitting devices have been widely developed for flat panel displays, and are moving fast toward solid state lighting (SSL) applications. Organic Light Emitting Diodes (OLEDs) comprise a cathode, a hole transporting layer, an emissive layer, an electron transporting layer, and an anode. Light emitted from an OLED device is the result of recombination of positive charges (holes) and negative charges (electrons) inside an organic (emissive) layer. The holes and electrons combine within a single molecule or a small cluster of molecules to generate excitons, which are molecules in an excited state, or groups of organic molecules bound together in an excited state. When the organic molecules release the required energy and return to their stable state, photons are generated. Organic materials which emit the photons are referred as an electro-fluorescent material or electro-phosphorescent material depending on the nature of the radiative process. Thus the OLED emissive compounds may be selected for their ability to absorb primary radiation and emit radiation of a desired wavelength. For blue emitters, for example, emission within principle emission bands of 440 to 490 nm may be desirable.

SSL applications may require a white OLED device to achieve greater than 1,500 lm brightness, a color rendering index (CRI) greater than 70, and an operating time greater than 100,000 hours at 100 lm/w. There are many approaches for generating white light from an OLED, but two common approaches are: direct combination of red, blue, and green light using either lateral patterning or vertical stacking of three emitters; and partial down conversion of blue light in combination with yellow phosphors. Both of these common approaches may be more effective if a highly efficient chemical- and photo-stable blue dye is employed. However, blue emitters may be less stable than dyes which emit other colors. Furthermore, there are very few blue emitting devices showing a CIE y value below 0.2 yet still with respectable efficiency. Thus, the development of deep blue emitters with good stability and high luminescence efficiency is desirable to effectively reduce power consumption and generate emission of different colors.

SUMMARY OF THE INVENTION

Some embodiments provide compounds that are useful in electronic devices, such as devices using compounds that absorb or emit deep blue light. Some embodiments provide compounds which comprise a series of 2, 3, or 4 aryl rings which may be directly connected or be interrupted by 1 or 2 oxygen atoms.

Some embodiments provide compounds represented by Formula 1:

$$R^1\text{—}Ar^1\text{—}X\text{—}Ar^2\text{—}Ar^3\text{-Het} \quad \text{(Formula 1)}$$

wherein $R^1$ is a $C_{1-10}O_{1-4}$ ether attaching at an oxygen atom or $-R^7-NR^8R^9$; wherein $R^7$ is a single bond, optionally substituted $C_{6-10}$ aryloxy, or optionally substituted $C_{6-10}$ aryl; and $R^8$ and $R^9$ are independently optionally substituted $C_{6-10}$ aryl, wherein $R^8$ and $R^9$ optionally link together form a third ring comprising N; $Ar^1$ and $Ar^2$ are independently optionally substituted aryl; X is O or a single bond; $Ar^3$ is optionally substituted aryl; or $Ar^3$ is a single bond; and Het is optionally substituted heteroaryl, including $C_{6-10}$ heteroaryl such as optionally substituted benzooxazolyl, optionally substituted benzothiazolyl, or optionally substituted benzoimidazolyl.

Some embodiments provide compounds represented by Formula 2:

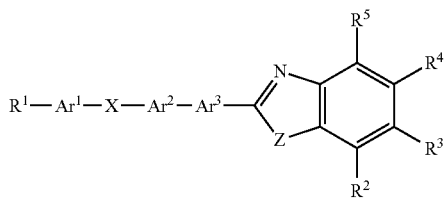

(Formula 2)

wherein $R^1$, $Ar^1$, $Ar^2$, $Ar^3$, and X are the same as described for Formula 1; Z is independently $NR^6$, O, or S, wherein $R^6$ is optionally substituted phenyl, optionally substituted $-CH_2$-phenyl, or optionally substituted (4-halophenyl)methyl; and $R^2$, $R^3$, $R^4$, and $R^5$ are independently H, optionally substituted $C_{6-30}$ aryl, $C_{1-10}$ alkyl, or $C_{1-10}$ alkoxy.

Some embodiments provide compounds represented by Formula 3:

(Formula 3)

wherein $R^1$ and Het are the same as described for Formula 1.

These compounds may be useful in devices which emit or absorb light, such as light in the deep blue region of the electromagnetic spectra. For example, some embodiments provide a light-emitting device comprising a compound disclosed herein.

Some embodiments provide a method of converting an electric potential difference to light comprising exposing a composition comprising a compound described herein to an electric potential difference to thereby produce light. Some embodiments are related to devices which convert an electric potential difference to light. These devices may operate by exposing a composition comprising a compound described herein to an electric potential difference to thereby produce light.

Some embodiments provide method of converting light to an electric potential difference comprising exposing a composition comprising a compound described herein to light to thereby produce an electric potential difference. Some embodiments are related to devices which convert light to an electric potential difference. These devices may operate by exposing a composition comprising a compound described herein to light to thereby produce an electric potential difference.

Some embodiments provide a light-emitting device, comprising a light-emitting layer comprising a compound disclosed herein.

These and other embodiments are described in greater detail below.

BRIEF DESCRIPTION OF THE DRAWINGS

FIG. 3 is a graph depicting the current density (mA/cm2) and brightness (cd/m2) of an embodiment of a device of FIG. 1 as a function of driving voltage.

FIG. 4 is a graph depicting the External Quantum Efficiency (EQE) of an embodiment of an organic light-emitting device of FIG. 1, as a function of current density.

FIG. 5 is a graph depicting the luminous efficiency (Cd/A) and power efficiency (lm/W) of an embodiment of an organic light-emitting device of FIG. 1, as a function of current density (mA/cm2).

FIG. 8 is a graph depicting the current density (mA/cm2) and brightness (cd/m2) of an embodiment of a device of FIG. 6 as a function of driving voltage.

FIG. 9 is a graph depicting the External Quantum Efficiency (EQE) of an embodiment of an organic light-emitting device of FIG. 6, as a function of current density.

FIG. 10 is a graph depicting the luminous efficiency (Cd/A) and power efficiency (lm/W) of an embodiment of an embodiment of an organic light-emitting device of FIG. 6, as a function of current density (mA/cm2).

DETAILED DESCRIPTION

Figure 2:
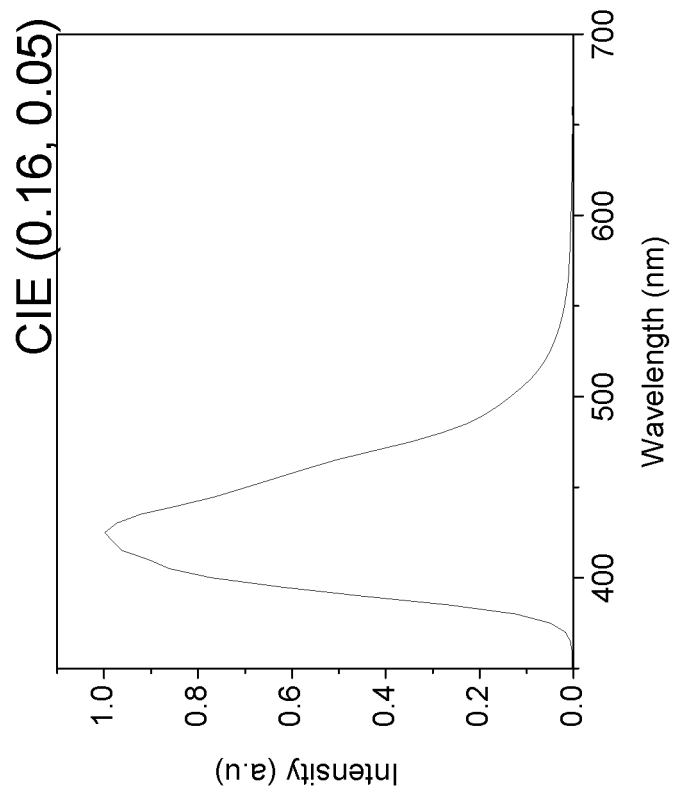
FIG. 2 is a graph depicting the electroluminescence spectrum and CIE coordinates of an embodiment of an organic light-emitting device of FIG. 1.

Unless otherwise indicated, when a chemical structural feature such as alkyl or aryl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent is a halogen, or has from 1-20 carbon atoms, from 1-10 carbon atoms, or has a molecular weight of less than about 500, about 300, or about 200. In some embodiments, the substituent has at least 1 carbon atom or at least 1 heteroatom, and has about 0-10 carbon atoms and about 0-5 heteroatoms independently selected from: N, O, S, F, Cl, Br, I, and combinations thereof. In some embodiments, each substituent consists of about 0-20 carbon atoms, about 0-47 hydrogen atoms, about 0-5 oxygen atoms, about 0-2 sulfur atoms, about 0-3 nitrogen atoms, about 0-1 silicon atoms, about 0-7 fluorine atoms, about 0-3 chlorine atoms, about 0-3 bromine atoms, and about 0-3 iodine atoms. Examples include, but are not limited to, alkyl, alkenyl, alkynyl, carbazolyl, cycloalkyl, cycloalkenyl, cycloalkynyl, aryl, diarylamino, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

The term "electron-donating substituent" has the ordinary meaning known to one of ordinary skill in the art. In some embodiments, the electron-donating substituent is a halogen, or has about 1-20 carbon atoms, about 1-10 carbon atoms, or has a molecular weight of less than about 500, about 300, or about 200. In some embodiments, the electron-donating substituent has at least 1 carbon atom or at least 1 heteroatom, and has about 0-10 carbon atoms and about 0-5 heteroatoms independently selected from: N, O, S, and combinations thereof. In some embodiments, the electron-donating substituent is an electron donor with respect to a phenyl ring to which it is attached. Some examples of electron-donating substituents may include, but are not limited to: alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxyl, aryloxy, O-ester, mercapto, alkylthio, arylthio, O-carbamyl, N-carbamyl, O-thiocarbamyl, N-thiocarbamyl, N-amido, O-carboxy, silyl, and amino.

The term "electron-withdrawing substituent" has the ordinary meaning known to one of ordinary skill in the art. In some embodiments, the electron-withdrawing substituent is a halogen, or has about 1-20 carbon atoms, about 1-10 carbon atoms, or has a molecular weight of less than about 500, about 300, or about 200. In some embodiments, the electron-donating substituent has at least 1 carbon atom or at least 1 heteroatom, and has about 0-10 carbon atoms and about 0-5 heteroatoms independently selected from: N, O, S, F, Cl, and combinations thereof. In some embodiments, the electron-withdrawing substituent is electron withdrawing with respect to a phenyl ring to which it is attached. Some examples of electron-withdrawing substituents may include, but are not limited to: acyl, C-ester, cyano, F, Cl, carbonyl, C-amido, thiocarbonyl, C-carboxy, protected C-carboxy, isocyanato, thiocyanato, isothiocyanato, nitro, sulfinyl, sulfonyl, perflouoralkyl, trihalomethanesulfonyl, and trihalomethanesulfonamido.

The term "aryl" as used herein refers to an aromatic ring or ring system. Exemplary non-limiting aryl groups are phenyl, naphthyl, etc. "$C_{x-y}$ aryl" refers to aryl where the ring or ring system has x-y carbon atoms. The indicated number of carbon atoms for the ring or ring system does not include or limit the number of carbon atoms in any substituents attached to the ring or ring system. Examples include, but are not limited to, optionally substituted phenyl, optionally substituted naphthyl, optionally substituted anthracenyl, optionally substituted p-interphenylene, optionally substituted 1,4-internaphthylene, and optionally substituted 9,10-interanthracenylene. These are shown below in their unsubstituted forms. However, any carbon not attached to the remainder of the molecule may optionally have a substituent.

The term "heteroaryl" refers to "aryl" which has one or more heteroatoms in the ring or ring system. "$C_{x-y}$ heteroaryl" refers to heteroaryl where the ring or ring system has x-y carbon atoms. The indicated number of carbon atoms for the ring or ring system does not include or limit the number of carbon atoms in any substituents attached to the ring or ring system. Examples of "heteroaryl" may include, but are not limited to, pyridinyl, furyl, thienyl, oxazolyl, thiazolyl, imidazolyl, indolyl, quinolinyl, benzofuranyl, benzothienyl, benzooxazolyl, benzothiazolyl, benzoimidazolyl, etc.

The term "diarylamino" as used herein refers to a moiety comprising a nitrogen atom which attaches to the remainder of the molecule (e.g. $Ar^1$), and the nitrogen atom is also directly attached to two optionally substituted aryl groups, the term aryl being described above. "$C_{x-y}$ diarylamino" as used herein refers a total number of carbon atoms in the range x-y in the two aryl rings. The indicated number of carbon atoms for the aryl rings does not include or limit the number of carbon atoms in any substituents attached to the ring or ring system. Examples include, but are not limited to, diphenyl amine (such as unsubstituted diphenyl amine or substituted diphenyl amine, e.g. phenyl(methylphenyl)amine, ditolyl amine).

The term "diarylaminophenoxy" as used herein refers to an optionally substituted phenoxy moiety (i.e. optionally substituted —O-phenyl), wherein the phenyl has an optionally substituted diarylamino substituent. "$C_{x-y}$ diarylaminophenoxy" as used herein refers a total number of carbon atoms in the range of x-y in the two aryl rings and in the phenyl ring. The indicated number of carbon atoms for the aryl rings does not include or limit the number of carbon atoms in any substituents attached to the ring or ring system. Examples include, but are not limited to, p-carbazolylphenoxy (such as unsubstituted p-carbazolylphenoxy, or p-carbazolylphenoxy substituted with 1, 2, 3, or 4 methyl substituents, etc.), p-diphenylaminophenoxy (such as unsubstituted p-diphenylaminophenoxy, or p-diphenylaminophenoxy substituted with 1, 2, 3, or 4 methyl substituents, etc.).

The names for several moieties used herein are indicated with the corresponding structures below. For any of these moieties, any carbon atom not attached to the remainder of the molecule, or any NH nitrogen, may optionally have a substituent.

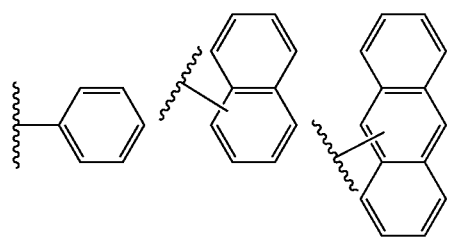

phenyl        naphthyl        anthracenyl

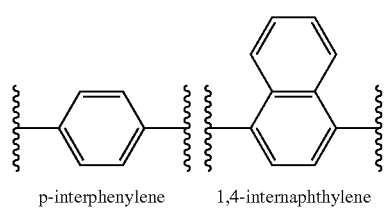

p-interphenylene        1,4-internaphthylene

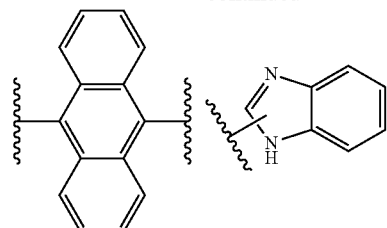

9,10-interanthracenylene        benzoimidazolyl

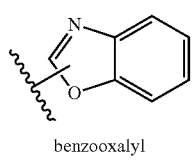

benzooxalyl

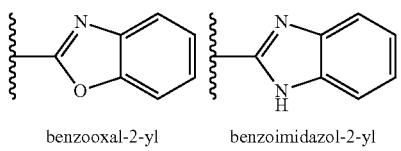

benzooxal-2-yl        benzoimidazol-2-yl

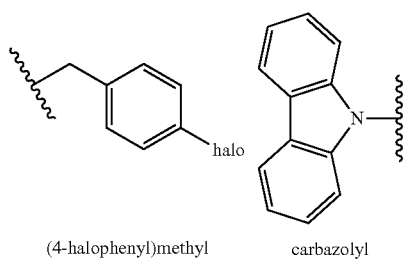

(4-halophenyl)methyl        carbazolyl

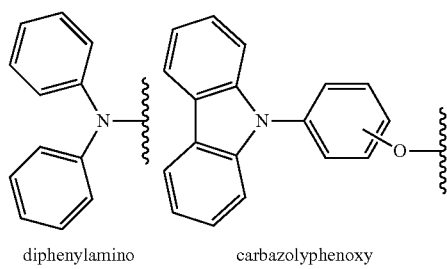

diphenylamino        carbazolyphenoxy

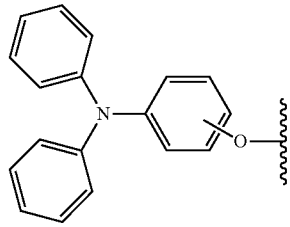

diphenylaminophenoxy

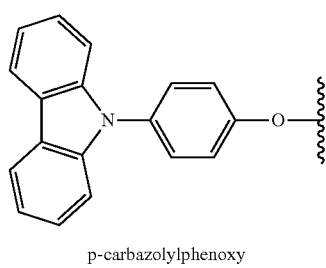

p-carbazolylphenoxy

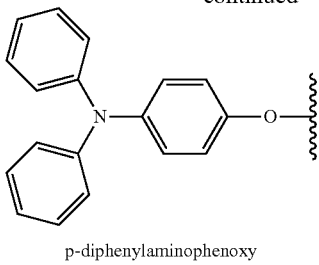

p-diphenylaminophenoxy

The term "alkyl" as used herein refers to a moiety comprising carbon and hydrogen containing no double or triple bonds. Alkyl may be linear, branched, cyclic, or a combination thereof, and contain from one to thirty-five carbon atoms. Examples of alkyl groups include but are not limited to methyl, ethyl, propyl, isopropyl, cyclopropyl, n-butyl, isobutyl, tent-butyl, cyclobutyl, pentyl isomers, cyclopentane, hexyl isomer, cyclohexane, and the like. The term "linear alkyl" as used herein refers to —$(CH_2)_qCH_3$, where q is 0-34. The term "$C_{1-10}$ alkyl" as used herein refers to alkyl having from 1 to 10 carbon atoms such as methyl, ethyl, propyl isomers, butyl isomers, cyclobutyl isomers, pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc. The term "alkylene" is a subgenus of "alkyl" and refers to a divalent alkyl moiety, e.g. —$CH_2$—, etc.

The term "ether" as used herein refers to a moiety comprising carbon, hydrogen, and single bonded oxygen, i.e. —O—, provided that —O—O— is not present. The phrase "$C_{1-10}O_{1-4}$ ether" refers to ether having from 1-10 carbon atoms and 1-4 oxygen atoms. The phrase "attaching at an oxygen atom" refers to a situation where the atom of the ether moiety which attaches to the rest of the structure (e.g. $Ar^1$) is an oxygen atom. Examples include alkoxy, polyalkylene oxide, etc. The term "alkoxy" as used herein refers to an ether of the formula —O-alkyl. The term "$C_{1-10}$ alkoxy" as used herein refers to alkoxy wherein the alkyl is $C_{1-10}$ alkyl as described above. The term "polyalkylene oxide" refers to an ether comprising a repeating —(O-alkylene)-unit, e.g. —$(OCH_2CH_2)_n$—OH, or —$(OCH_2CH_2)_n$—$OCH_3$, wherein n is 1-4. In some embodiments, the ether attaching at an oxygen atom may be selected from the group consisting of: —O—$R^V$, —O—$R^W$—O—$R^X$, —O—$R^W$—O—$R^Y$—O—$R^X$, or —O—$R^W$—O—$R^Y$—O—$R^Z$—O—$R^X$, wherein $R^V$ is $C_{1-10}$ alkyl, $R^W$ is $C_{2-10}$ alkyl, $R^Y$ is $C_{2-8}$ alkyl, and $R^Z$ is $C_{2-6}$ alkyl, and $R^X$ is H or $C_{2-8}$ alkyl, provided that the ether has from 1, 2, 3, 4, 5, 6, 7, 8, 9, or 10 carbon atoms.

The term "work function" has the ordinary meaning known to one of ordinary skill in the art. In some embodiments, the "work function" of a metal refers to a measure of the minimum energy required to extract an electron from the surface of the metal.

The term "high work function metal" has the ordinary meaning known to one of ordinary skill in the art. In some embodiments, a "high work function metal" is a metal or alloy that easily injects holes and typically has a work function greater than or equal to 4.5.

The term "low work function metal" has the ordinary meaning known to one of ordinary skill in the art. In some embodiments, a "low work function metal" is a metal or alloy that easily loses electrons and typically has a work function less than 4.3.

The expression "white light-emitting" has the ordinary meaning known to one of ordinary skill in the art. In some embodiments, a material is white light-emitting if it emits white light. In some embodiments, white light is light having the approximate CIE color coordinates (X=1/3, Y=1/3). The CIE color coordinates (X=1/3, Y=1/3) may be defined as the achromatic point. The X and Y color coordinates may be weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

The term "deep blue emitting" has the ordinary meaning known to one of ordinary skill in the art. In some embodiments, a material is "deep blue emitting" if it emits deep blue light. Deep blue light is light having the approximate CIE color coordinates (X=[0.14], Y=[0.08], CIE 1931).

Some embodiments provide compounds that are useful as deep blue emitters. Formula 1 and Formula 2 represent examples of such compounds. With respect to Formula 1 and Formula 2, X may be O or a single bond. Thus, some embodiments are related to compounds represented by one of Formulas 1a, 1b, 2a, and 2b.

$R^1$—$Ar^1$—O—$Ar^2$—$Ar^3$-Het    (Formula 1a)

$R^1$—$Ar^1$—$Ar^2$—$Ar^3$-Het    (Formula 1b)

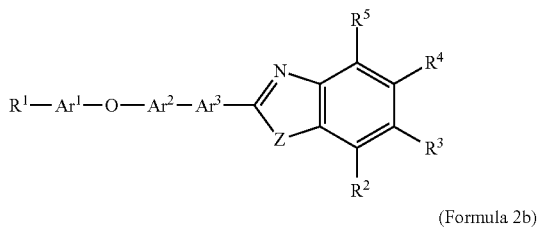

(Formula 2a)

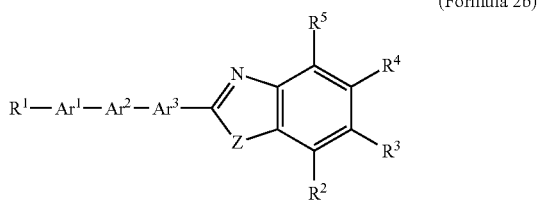

(Formula 2b)

With respect to Formula 1, Formula 1a, Formula 1b, Formula 2, Formula 2a and Formula 2b, $Ar^3$ may be optionally substituted 1,4-interarylene or $Ar^3$ may be a single bond. Thus, some embodiments are related to compounds represented by Formulas 1c and 2c.

$R^1$—$Ar^1$—$Ar^2$-Het    (Formula 1c)

(Formula 2c)

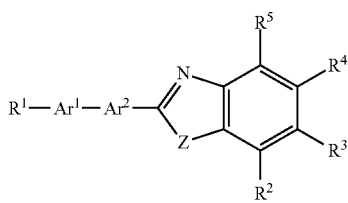

Furthermore, some embodiments are related to compound represented by Formula 4.

(Formula 4)

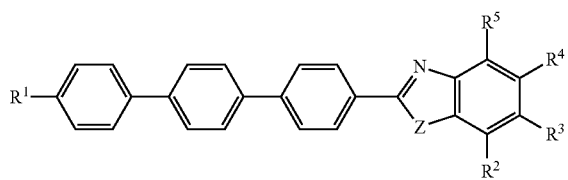

Some embodiments provide compounds represented by Formula 5, Formula 6, Formula 7, Formula 8, or Formula 9:

(Formula 5)

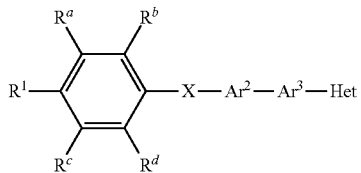

(Formula 6)

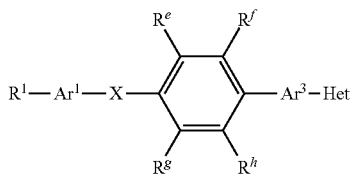

(Formula 7)

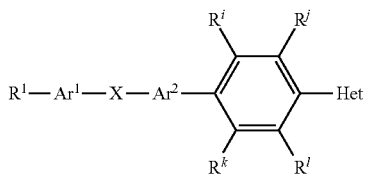

(Formula 8)

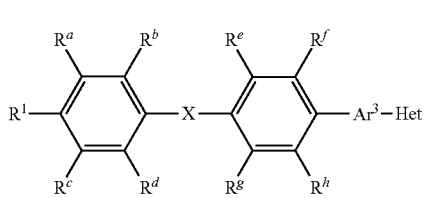

(Formula 9)

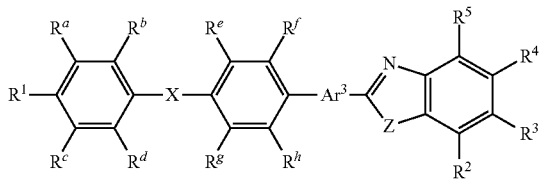

With respect to any relevant formula above, Het may be optionally substituted heteroaryl, such as optionally substituted $C_{6-10}$ heteroaryl, including, but not limited to, optionally substituted benzooxazolyl, optionally substituted benzothiazolyl, optionally substituted benzoimidazolyl, optionally substituted benzooxazol-2-yl, optionally substituted benzothiazol-2-yl, optionally substituted benzoimidazol-2-yl, etc.

With respect to any relevant formula above, $Ar^1$ and $Ar^2$ may independently be optionally substituted aryl, and $Ar^3$ may be optionally substituted aryl; or $Ar^3$ may be a single bond. $Ar^1$, $Ar^2$, $Ar^3$ (if present), and Het are independently optionally substituted. For example, in some embodiments, $Ar^1$ may be unsubstituted, or may have 1, 2, 3, or 4 substituents. In some embodiments, $Ar^2$ may be unsubstituted, or may have 1, 2, 3, or 4 substituents. In some embodiments, $Ar^3$ may be unsubstituted, or may have 1, 2, 3, or 4 substituents. In some embodiments, Het may be unsubstituted, or may 1, 2, 3, or 4 substituents.

Some substituents of any of $Ar^1$, $Ar^2$, $Ar^3$ (if present), and Het may include, but are not limited to, $C_{1-10}$ alkyl such as methyl, ethyl, propyl isomers (e.g. n-propyl and isopropyl), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, heptyl isomer, cycloheptyl isomers, etc; alkoxy such as —$OCH_3$, —$OC_2H_5$, —$OC_3H_7$, —$OC_4H_9$, —$OC_5H_{11}$, —$OC_6H_{13}$, —$OC_7H_{15}$, etc.; halo, such as F, Cl, Br, I, etc.; $C_{1-10}$ haloalkyl, including perfluoroalkyl such as —$CF_3$, —$C_2F_5$, —$C_3F_7$, —$C_4F_9$, etc.; $C_{1-10}$ acyl such as formyl, acetyl, benzoyl, etc.; $C_{1-10}$ amides attaching at the carbonyl or nitrogen atom such as —$NCOCH_3$, —$CONHCH_2$, etc.; $C_{1-10}$ esters attaching at the carbonyl or oxygen atom such as —$OCOCH_3$, —$CO_2CH_2$, etc.; $C_{1-10}$ carbamates attaching at the nitrogen atom or oxygen atom; cyano; cyanate; isocyanate; nitro; etc.

Also with respect to any relevant formula above, in some embodiments Het may comprise at least one electron-withdrawing substituent. In some embodiments, the electron-withdrawing substituent is a better electron withdrawer than a hydrogen atom. Examples include, but are not limited to, cyano, cyanate, isocyanate, nitro, F, Cl, perfluoralkyl, acyl, esters that attach at the carbonyl, or amides that attach at the carbonyl.

Also with respect to any relevant formula above, in some embodiments $Ar^1$ may comprise at least one electron-donating substituent. In some embodiments, the electron-donating substituent may be a better electron donor than a hydrogen atom. Examples include, but are not limited to alkyl, ethers attaching at an oxygen atom such as alkoxy, aryloxy or polyalkylene oxide, amino (e.g. —NR'R", wherein R' and R" are independently H or alkyl), hydroxyl, etc.

Also with respect to any relevant formula above, $R^1$ is a $C_{1-10}O_{1-4}$ ether attaching at an oxygen atom or —$R^7$—$NR^8R^9$; wherein $R^7$ is a single bond, optionally substituted $C_{6-10}$ aryloxy, or optionally substituted $C_{6-10}$ aryl; and $R^8$ and $R^9$ are independently optionally substituted $C_{6-10}$ aryl, wherein R⁸ and R⁹ optionally link together form a third ring comprising N. In some embodiments each of R¹, R⁷, R⁸, and R⁹ may independently be unsubstituted, or may have 1, 2, 3, 4, or 5 substituents. In some embodiments, the substituents of R¹, R⁷, R⁸, and R⁹ may be F, Cl, —R', —OR', or —NR'R", wherein each R' and R" is independently H, optionally substituted phenyl, $C_{1-12}$ alkyl, or $C_{1-6}$ alkyl.

In some embodiments, R¹ may be optionally substituted $C_{12-30}$ diarylamino, such as optionally substituted diphenylamino, optionally substituted phenylnapthylenamino, optionally substituted phenylanthracenamino, etc.; optionally substituted carbazolyl; or a $C_{1-10}O_{1-4}$ ether attaching at an oxygen atom such as alkoxy (e.g. —OCH₃, —OC₂H₅, —OC₃H₇, —OC₄H₉, —OC₅H₁₁, —OC₆H₁₃, etc.), or polyalkylene oxide (e.g. —OCH₂CH₂OH, —OCH₂CH₂OCH₃, —(OCH₂CH₂)₂OH, —(OCH₂CH₂)₂OCH₃, —(OCH₂CH₂)₃OH, —(OCH₂CH₂)₃OCH₃, —(OCH₂CH₂)₄OH, —(OCH₂CH₂)₄OCH₃, etc). In some embodiments, R¹ is substituted $C_{12-30}$ diarylamino, optionally substituted carbazolyl, optionally substituted $C_{18-36}$ diarylaminophenoxy, optionally substituted carbazolylphenoxy, or a $C_{1-10}O_{1-4}$ ether attaching at an oxygen atom. In some embodiments, R¹ may be optionally substituted carbazolyl, optionally substituted diphenylamino, optionally substituted carbazolylphenoxy, optionally substituted p-carbazolylphenoxy, optionally substituted diphenylaminophenoxy, or optionally substituted p-diphenylaminophenoxy, or $C_{1-10}$ alkoxy. In some embodiments, R¹ may be methoxy,

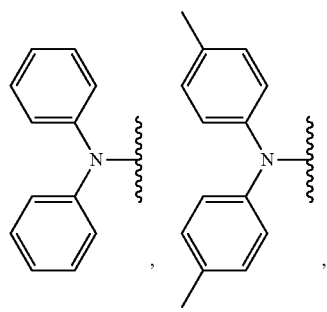

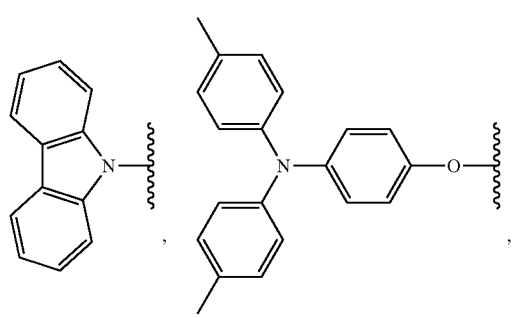

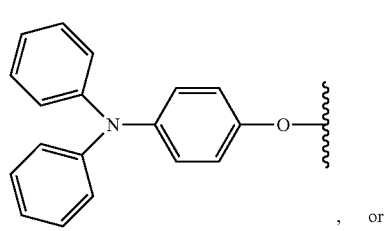

, or

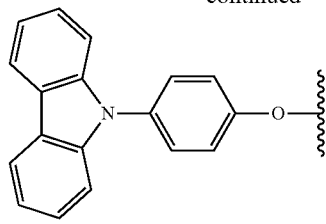

Also with respect to any relevant formula above, R², R³, R⁴, and R⁵ may independently be any substituents. In some embodiments, R², R³, R⁴, and R⁵ may be independently H, optionally substituted $C_{6-30}$ aryl; such as optionally substituted phenyl, $C_{1-10}$ alkyl, such as methyl, ethyl, propyl isomers (e.g. n-propyl and isopropyl), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, heptyl isomer, cycloheptyl isomers, etc or $C_{1-10}$ alkoxy, alkoxy such as —OCH₃, —OC₂H₅, —OC₃H₇, —OC₄H₉, —OC₅H₁₁, —OC₆H₁₃, —OC₇H₁₅, etc.

Also with respect to any relevant formula above, $R^a$, $R^b$, $R^c$, $R^d$, $R^e$, $R^f$, $R^g$, $R^h$, $R^i$, $R^j$, $R^k$, and $R^l$ may be any substituent. In some embodiments, $R^a$, $R^b$, $R^c$, $R^d$, $R^e$, $R^f$, $R^g$, $R^h$, $R^i$, $R^j$, $R^k$, and $R^l$ may be independently selected from $C_{1-10}$ alkyl and halo. In some embodiments, $R^a$, $R^b$, $R^c$, $R^d$, $R^e$, $R^f$, $R^g$, $R^h$, $R^i$, $R^j$, $R^k$, and $R^l$ may be independently selected from $C_{1-3}$ alkyl, F, and Cl.

Also with respect to any relevant formula above, in some embodiments at least one of Ar¹, Ar², and Ar³ (if present) may be optionally substituted p-interphenylene. In some embodiments, each of Ar¹, Ar², and Ar³ (if present) may independently be optionally substituted p-interphenylene. In some embodiments, Ar¹, Ar², and Ar³ (if present) may independently have 0, 1, or 2 substituents independently selected from $C_{1-3}$ alkyl, F, and Cl. In some embodiments, at least one of Ar¹, Ar², and Ar³ (if present) may be unsubstituted p-interphenylene. In some embodiments, each of Ar¹, Ar², and Ar³ (if present) may be unsubstituted p-interphenylene.

Also with respect to any relevant formula above, in some embodiments Z may be O, S, or NR⁶ wherein R⁶ is optionally substituted phenyl. In some of embodiments, Z may be O, S, or NR⁶ wherein R⁶ is optionally substituted phenyl; and R¹ may be optionally substituted diphenyl amine, optionally substituted carbazolyl, optionally substituted p-carbazolylphenoxy, or optionally substituted p-diphenylaminophenoxy.

Also with respect to any relevant formula above, in some embodiments R¹ is optionally substituted diphenyl amine or optionally substituted carbazolyl.

Also with respect to any relevant formula above, in some embodiments Ar³ is 1,4-interarylene having 0, 1, or 2 substituents independently selected from $C_{1-3}$ alkyl, F, and Cl. In some embodiments, Ar³ is 1,4-interarylene having 0, 1, or 2 substituents independently selected from $C_{1-3}$ alkyl, F, and Cl; and R¹ is optionally substituted diphenyl amine, or optionally substituted carbazolyl.

Also with respect to any relevant formula above, in some embodiments —Ar¹—X—Ar²—Ar³— is not

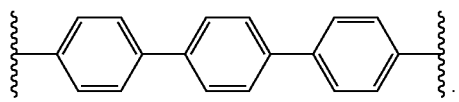
Some embodiments relate to optionally substituted Ring Systems 1-9.
(Ring System 1)
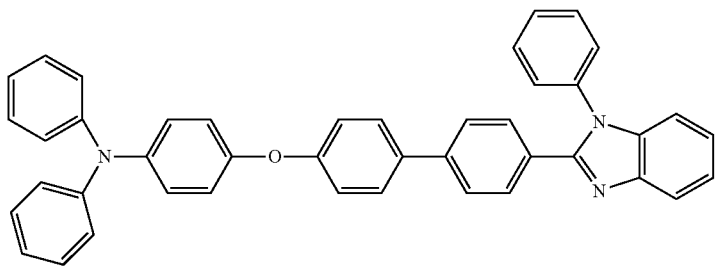
(Ring System 2)
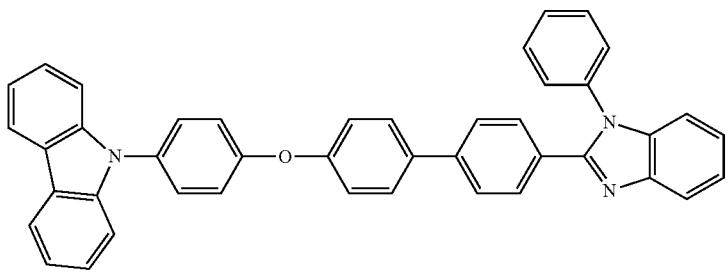
(Ring System 3)
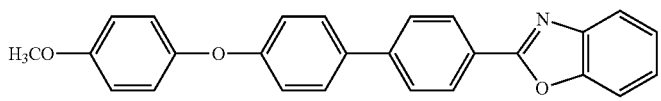
(Ring System 4)
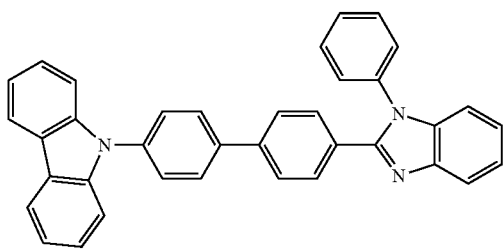
(Ring System 5)
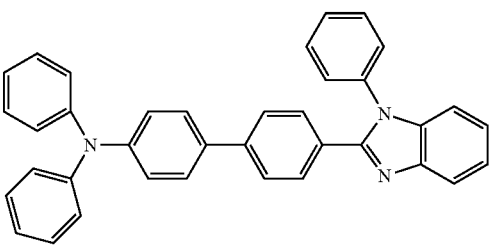
(Ring System 6)
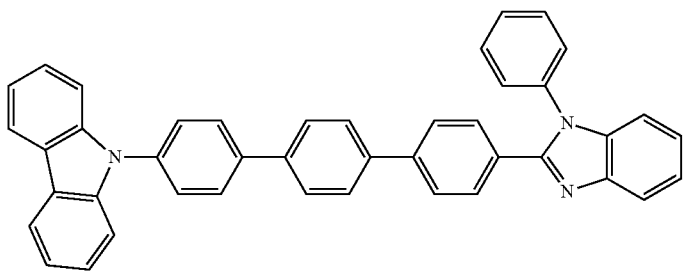

-continued
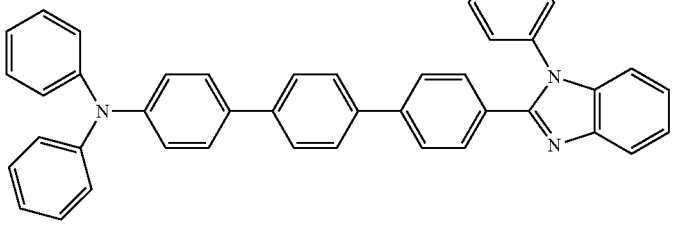
(Ring System 7)
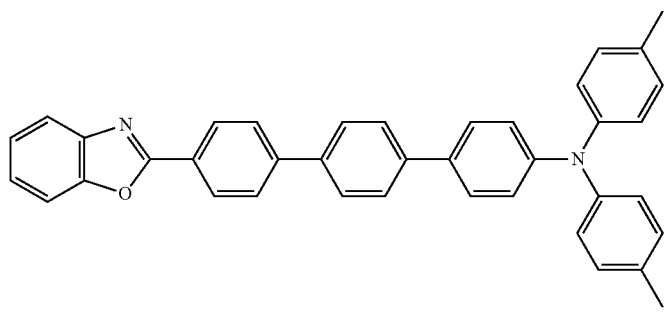
(Ring System 8)
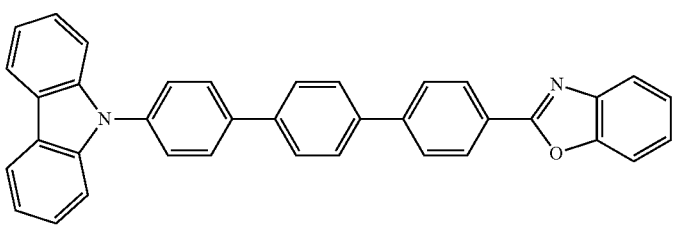
(Ring System 9)
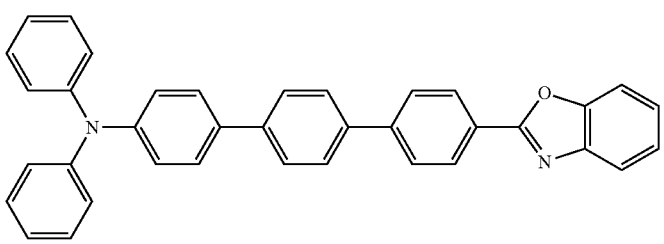
(Ring System 10)
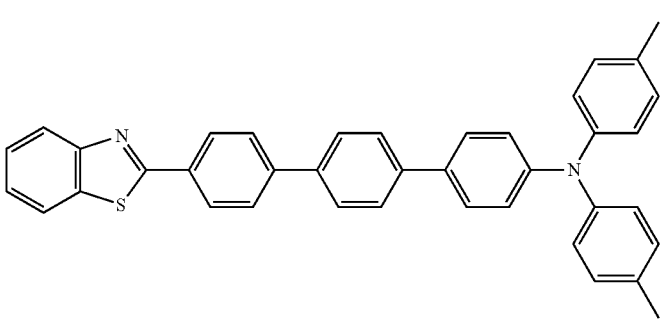
(Ring System 11)
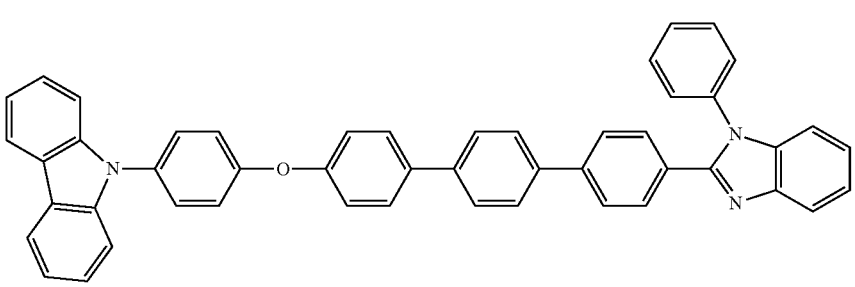
(Ring System 12)

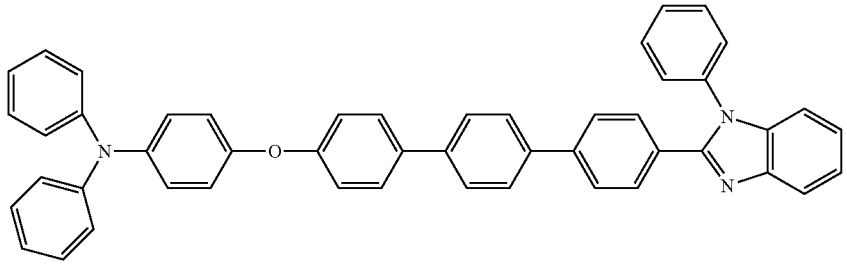

(Ring System 13)

In these embodiments, the ring systems may have any substituent described above, including those described with respect to $Ar^1$, $Ar^2$, $Ar^3$, and Het. In some embodiments, Ring Systems 1-7 may have 0, 1, 2, 3, 4, 5, or 6 substituents. In some embodiments, the substituents are independently selected from: $C_{1-6}$ alkyl, $C_{1-6}$ alkoxy, F, Cl, Br, and I.

Some embodiments relate to a compound selected from:

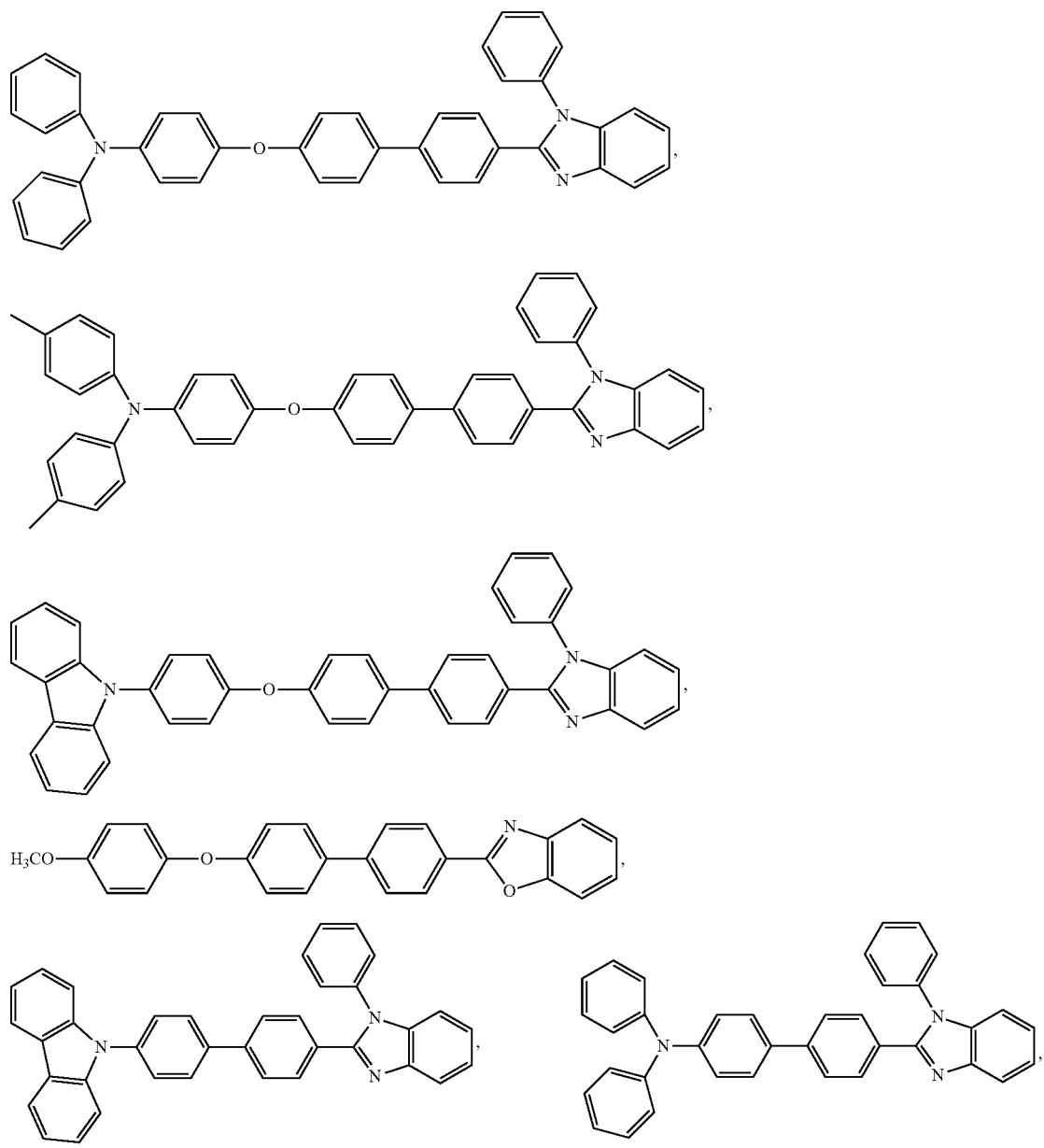

-continued
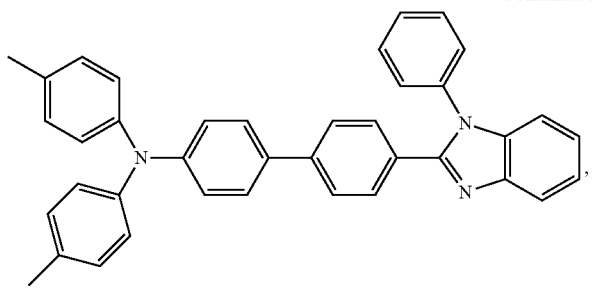
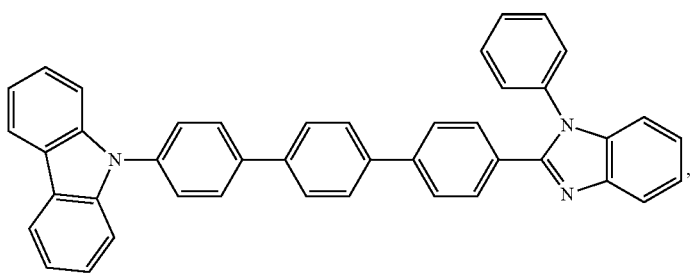
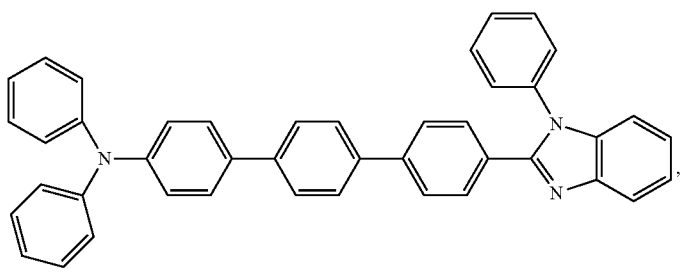
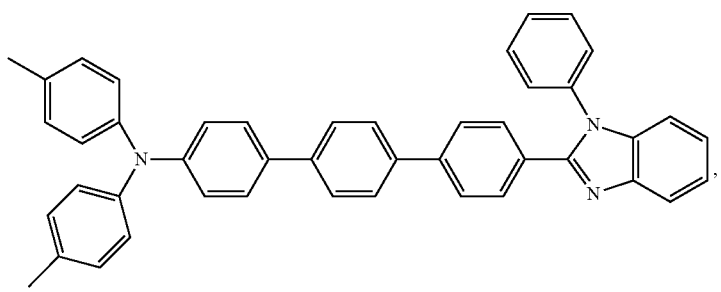
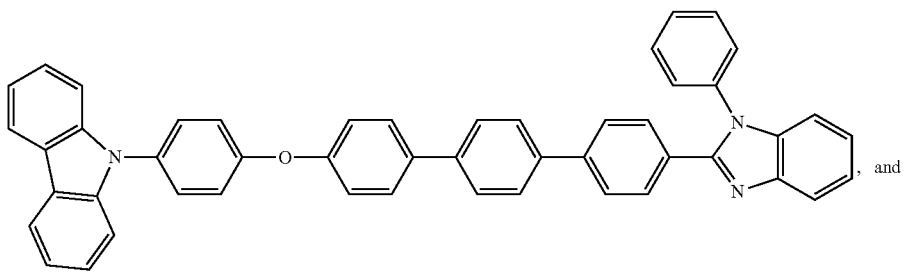, and
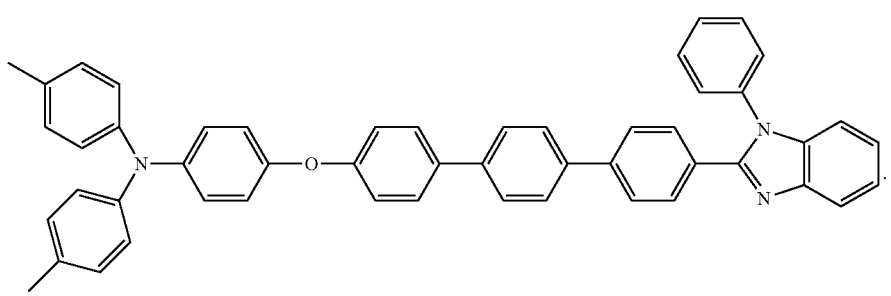

The compounds and compositions described herein can be incorporated into light-emitting devices in various ways. For example, an embodiment provides a light-emitting device comprising: an anode layer (e.g., an anode layer comprising a high work function metal); a cathode layer (e.g., a cathode layer comprising a low work function metal); and a light-emitting layer positioned the anode layer and the cathode layer. In some embodiments, the device is configured so that electrons can be transferred from the cathode to the light-emitting layer and holes can be transferred from the anode to the light-emitting layer. The light-emitting layer comprises the compounds and/or compositions disclosed herein.

An anode layer may comprise a conventional material such as a metal, mixed metal, alloy, metal oxide or mixed-metal oxide, or a conductive polymer. Examples of suitable metals include the metals in Groups 10, Group 11, and Group 12 transition metals. If the anode layer is to be light-transmitting, mixed-metal oxides of Groups 12, Group 13, and Group 14 metals or alloys thereof, such as zinc oxide, tin oxide, indium zinc oxide (IZO) or indium-tin-oxide (ITO) may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 11, Group 12, and Group 13 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

The amount of the compounds disclosed herein in the light-emitting composition can vary. In some embodiments, the light-emitting layer consists essentially of a compound disclosed herein. In other embodiments, the emissive layer comprises a host material and at least one of the emissive compounds disclosed herein. If there is a host material, the amount of the emissive compound with respect to the host material may be any amount suitable to produce adequate emission. In some embodiments, the amount of a compound disclosed herein in the light-emitting layer is in the range of from about 1% to about 100% by weight of the light-emitting layer. In embodiments where a compound disclosed herein is used as a host, the compound may be about 80% or about 90% to about 99% by weight, of the light-emitting layer. In embodiments where a compound disclosed herein is used as an emissive compound, the compound may be about 1% to about 10%, or alternatively, about 3% by weight of the light-emitting layer.

The thickness of the light-emitting layer may vary. In some embodiments, the light-emitting layer has a thickness in the range of from about 20 nm to about 150 nm, or from about 20 nm to about 200 nm.

The host in the emissive layer may be at least one of: one or more hole-transport materials, one or more electron-transport materials, and one or more ambipolar materials, which are materials understood by those skilled in the art to be capable of transporting both holes and electrons.

In some embodiments, the hole-transport material comprises at least one of an aromatic-substituted amine, a carbazole, a polyvinylcarbazole (PVK), e.g. poly(9-vinylcarbazole); N,N'-bis(3-methylphenyl)N,N'-diphenyl-[1,1'-biphenyl]-4,4'-diamine (TPD); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4"-Tris(N-(naphthylen-2-yl)-N-phenylamino)triphenylamine; 4,4',4'-tris(3-methylphenylphenylamino)triphenylamine (MTDATA); 4,4'-bis[N-(naphthyl)-N-phenyl-amino]biphenyl (α-NPD); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); poly(9-vinylcarbazole) (PVK); a benzidine; a phenylenediamine; a phthalocyanine metal complex; a polyacetylene; a polythiophene; a triphenylamine; an oxadiazole; copper phthalocyanine; N,N'N"-1,3,5-tricarbazoloylbenzene (tCP); N,N'-bis(4-butylphenyl)-N,N'-bis(phenyl)benzidine; mixtures thereof, and the like.

In some embodiments, the electron-transport material comprises at least one of 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenyl-benzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In some embodiments, the electron transport layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a mixture thereof.

In some embodiments, the device comprises no electron transport or hole transport layer. In some embodiments, the device consists essentially of the anode layer, the cathode layer, and the light-emitting layer. In other embodiments, the light-emitting device may further comprise a hole-transport layer disposed between the anode and the light-emitting layer. The hole-transport layer may comprise at least one hole-transport material. Suitable hole-transport materials may include those listed above in addition to any others known to those skilled in the art. In some embodiments, the light-emitting device may further comprise an electron-transport layer disposed between the cathode and the light-emitting layer. The electron-transport layer may comprise at least one electron-transport material. Suitable electron transport materials include those listed above and any others known to those skilled in the art.

If desired, additional layers may be included in the light-emitting device. These additional layers may include an electron injection layer (EIL), a hole blocking layer (HBL), an exciton blocking layer (EBL), and/or a hole injection layer (HIL). In addition to separate layers, some of these materials may be combined into a single layer.

In some embodiments, the light-emitting device can include an electron injection layer between the cathode layer and the light emitting layer. A number of suitable electron injection materials are known to those skilled in the art. Examples of suitable material(s) that can be included in the electron injection layer include but are not limited to, an optionally substituted compound selected from the following: aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In some embodiments, the electron injection layer is aluminum quinolate ($Alq_3$), 2-(4-biphenylyl)-5-(4-tert-butylphenyl)-1, 3,4-oxadiazole (PBD), phenanthroline, quinoxaline, 1,3,5-tris[N-phenylbenzimidazol-z-yl]benzene (TPBI), or a derivative or a combination thereof.

In some embodiments, the device can include a hole blocking layer, e.g., between the cathode and the light-emitting layer. Various suitable hole blocking materials that can be included in the hole blocking layer are known to those skilled in the art. Suitable hole blocking material(s) include but are not limited to, an optionally substituted compound selected from the following: bathocuproine (BCP), 3,4,5-triphenyl-1, 2,4-triazole, 3,5-bis(4-tert-butyl-phenyl)-4-phenyl4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton blocking layer, e.g., between the light-emitting layer and the anode. In an embodiment, the band gap of the material(s) that comprise exciton blocking layer is large enough to substantially prevent the diffusion of excitons. A number of suitable exciton blocking materials that can be included in the exciton blocking layer are known to those skilled in the art. Examples of material(s) that can compose an exciton blocking layer include an optionally substituted compound selected from the following: aluminum quinolate ($Alq_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole injection layer, e.g., between the light-emitting layer and the anode. Various suitable hole injection materials that can be included in the hole injection layer are known to those skilled in the art. Exemplary hole injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenyl-benzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper. Hole-injection materials, while still being able to transport holes, may have a hole mobility substantially less than the hole mobility of conventional hole transport materials.

Those skilled in the art recognize that the various materials described above can be incorporated in several different layers depending on the configuration of the device. In one embodiment, the materials used in each layer are selected to result in the recombination of the holes and electrons in the light-emitting layer. An example of a device configuration that incorporates the various layers described herein is illustrated schematically in FIG. 1. The electron injection layer (EIL), electron transport layer (ETL), hole blocking layer (HBL), exciton blocking layer (EBL), hole transport layer (HTL), and hole injection layer (HIL) can be incorporated in the light-emitting device using methods known to those skilled in the art (e.g., vapor deposition).

The emissive compositions may be prepared by adapting methods known in the art for other emissive compositions. For example, the emissive compositions may be prepared by dissolving or dispersing the emissive compound in a solvent and depositing the compound on the appropriate layer of the device. The liquid may be a single phase, or may comprise one or more additional solid or liquid phases dispersed within the liquid. The solvent may then be allowed to evaporate, or the solvent may be removed via heat or vacuum, to provide an emissive composition. If a host is present, it may be dissolved or dispersed in the solvent with the emissive device and treated as explained above. Alternatively, the compound may be added to a molten or liquid host material, which is then allowed to solidify to provide a viscous liquid or solid emissive composition.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein can be deposited on the anode. The cathode layer, comprising a low work functioning metal (e.g., Mg:Ag), can then be deposited, e.g., vapor evaporated, onto the light-emitting layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

In some embodiments, the light-emitting device (e.g., OLED) is configured by a wet process such as a process that comprises at least one of spraying, spin coating, drop casting, inkjet printing, screen printing, etc. Some embodiments provide a composition which is a liquid suitable for deposition onto a substrate. The liquid may be a single phase, or may comprise one or more additional solid or liquid phases dispersed in it. The liquid typically comprises a light-emitting compound, a host material disclosed herein and a solvent.

EXAMPLES

Example 1

General Synthetic Methods

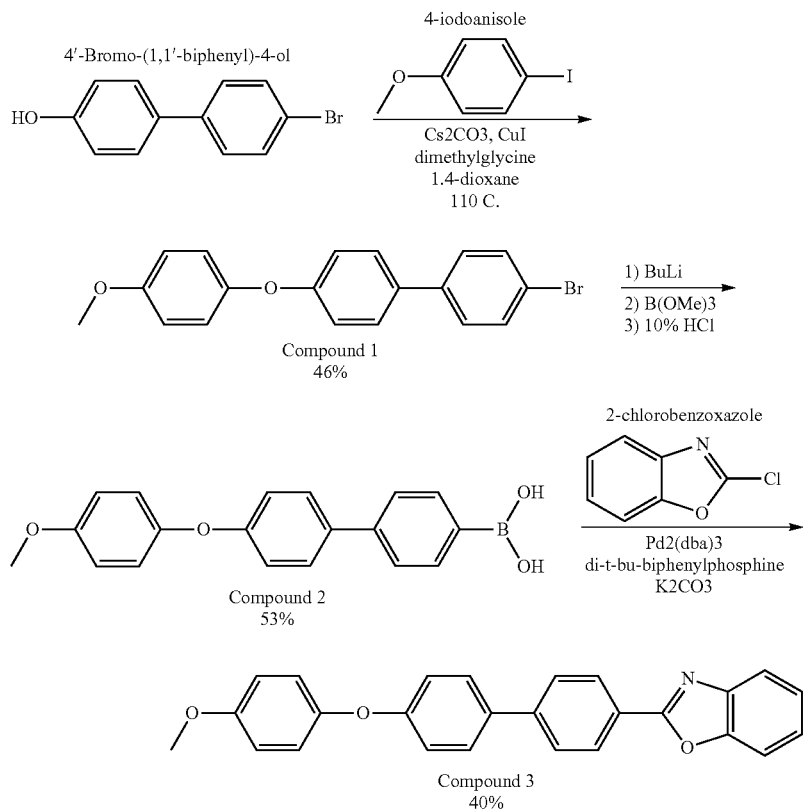

Example 1.1.1

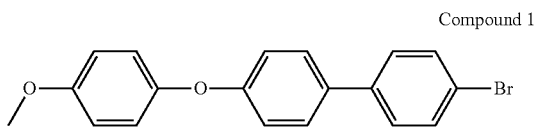

Compound 1

A mixture of 4'-Bromo-(1,1'-biphenyl)-4-ol (10.0 g, 40.1 mmol), 4-iodoanisole (18.72 g, 80.0 mmol), cesium carbonate (26.1 g, 80.2 mmol), copper iodide (760 mg, 4.0 mmol), dimethylglycine hydrochloride (1.68 g, 12.0 mmol), and anhydrous 1,4-dioxane (50 mL) was purged via freeze-pump-thaw method. The resulting mixture was heated to 110° C. overnight. After cooling, the resulting mixture was poured into ethyl acetate (300 mL), and stirred at 40° C. for 30 min; and the resulting solids were filtered off. The filtrate was dried under vacuum to give ivory solids. The ivory solids were washed with a mixture of ethyl acetate and methanol to give pure product (Compound 1); 6.5 g, 46% yield; confirmed by HNMR

Example 1.1.2

Compound 1 (2 g, 5.63 mmol) was dissolved in anhydrous tetrahydrofuran (30 mL), and the resulting solution was cooled to −78° C. Butyllithium (3.43 mL of a 1.6 M solution, 5.5 mmol) was added dropwise and the solution was stirred at −78° C. for three hours. Trimethyl borate (0.572 mL, 5.5 mmol) was added slowly, and the resulting mixture was stirred for three hours at room temperature. Saturated ammonium chloride solution (45 mL) (alternatively, 10% HCl solution used) was added and the mixture was stirred overnight at room temperature. The desired product extracted with ethyl acetate (2×100 mL). The organic layer from the extraction was dried under vacuum. Precipitation in DCM/methanol gave white solids. The white solids were filtered and washed with methanol. The filtrate was dried to give relatively pure product (Compound 2); 1.2 g, 53% yield; relatively pure by HNMR.

Example 1.1.3

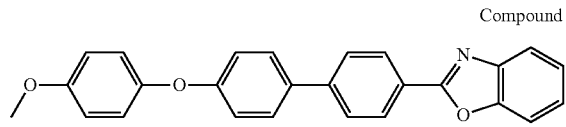

Compound 3

A mixture of Compound 2 (100 mg, 0.31 mmol), 2-chlorobenzoxazole (50 mg, 0.33 mmol), Pd(OAc)2 (3.5 mg, 0.015 mmol), di-t-butyl-biphenylphosphine (9 mg, 0.03 mmol) and KF (54 mg, 0.93 mmol) in 1,4-dioxane (5 mL) was degassed then heated at 110° C. for 36 hours under argon. After cooling to room temperature, the mixture was poured into dichloromethane (100 mL). After filtration, the filtrate was loaded on silica gel column and purified by flash chromatography (heaxanes/ethyl acetate 10:1 to 5:1). A white solid was obtained (40 mg, 40%) as the desired product (Compound 3), which was confirmed by LCMS (calculated for $C_{26}H_{20}NO_3$ (M+H): 394; found m/e=394) and HNMR.

Example 1.2

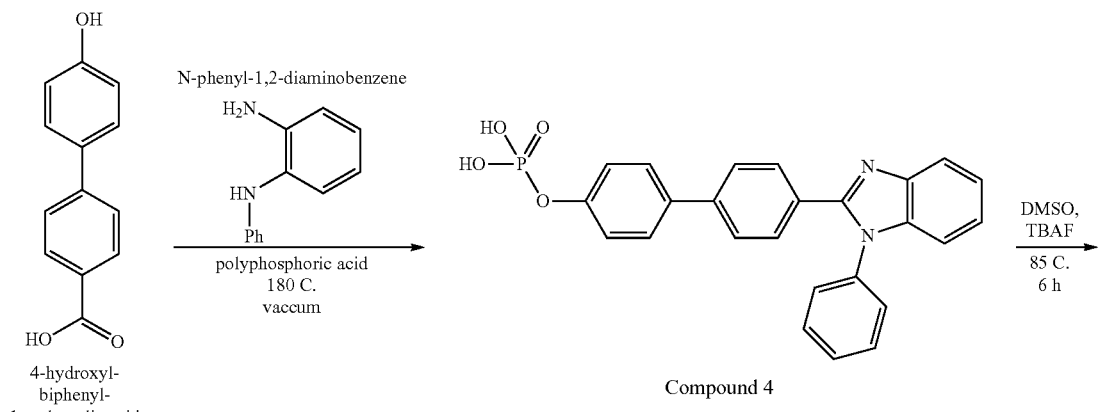

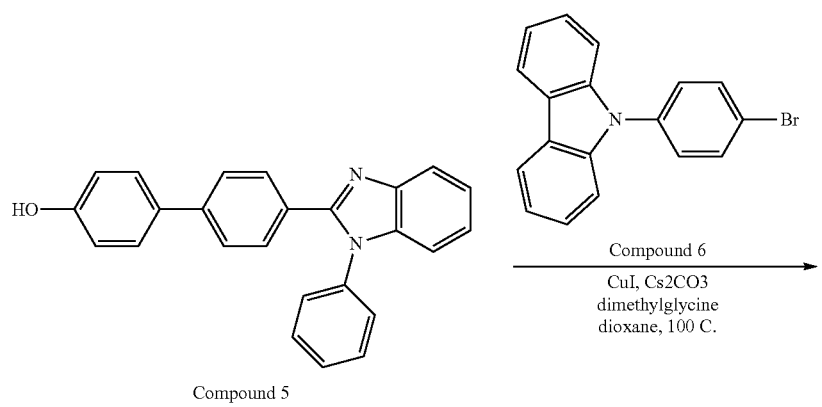

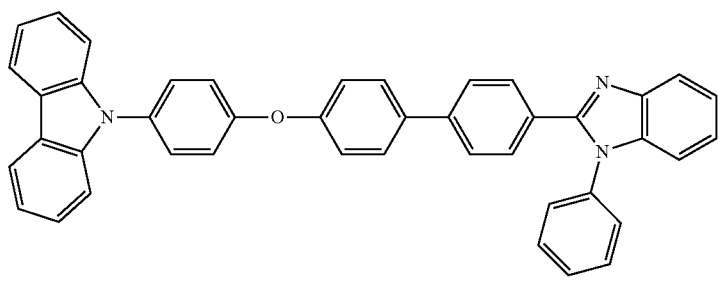

Compound 7

Example 1.2.1

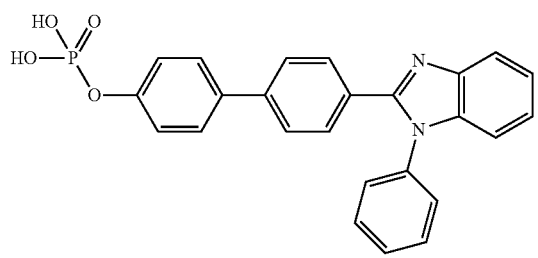

Compound 4

A mixture of 4-hydroxylbiphenyl-1-carboxylic acid (2.14 g, 10 mmol) and N-phenyl-1,2-diaminobenzene (1.84 g, 10 mmol) in polyphosphoric acid (10 ml) was degassed by vacuum then heated at 180° C. at 10 torr overnight. After cooling to room temperature, the mixture was poured into water. Filtration and washing with water gave a dark solid (6.8 g, 84%) as the desired product (Compound 4), which was confirmed by LCMS (calculated for $C_{25}H_{18}N_2O_4P$ (M−H): 441, found m/e: 441).

Example 1.2.2

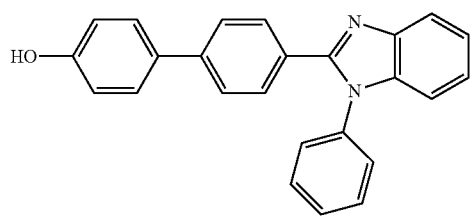

Compound 5

To a solution of Compound 4 (3.6 g, 8 mmol) in DMSO (20 mL), was added tetrabutylammonium fluoride (1 M in THF, 18 mL). The mixture was heated at 85° C. for 6 hours. Water (50 mL) was added to the hot solution, followed by 5 mL concentrated HCl. The mixture was stirred for 5 min and allowed to cool down to room temperature. Filtration and drying under vacuum at 110° C. overnight afford a black solid (1.6 g, 55%) as desired product (Compound 5), which was confirmed by LCMS (calculated for $C_{25}H_{17}N_2O$ (M−H): 361; found m/e=361).

Example 1.2.3

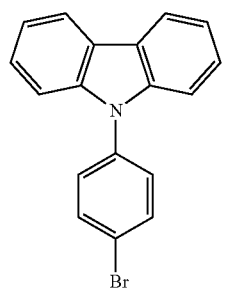

Compound 6

A mixture of carbazole (7.0 g, 42.2 mmol), 4-bromo-iodobenzene (17.9 g, 63.3 mmol), copper (13.6 g, 214 mmol), 18-crown-6 (4.36 g, 16.48 mmol), potassium carbonate (29.5 g, 214 mmol), and anhydrous N,N-dimethylformamide (50 mL) was degassed for 30 minutes. The mixture was heated to 150° C. overnight under argon. After cooling, the mixture was poured into DCM (400 mL) and the subsequent mixture was filtered. The filtrate was concentrated under vacuum, and hexane was added to precipitate out 18-crown-6, which was filtered off. The filtrate was loaded on silica gel. A flash column (silica, 100% hexane) and reprecipitation in DCM/hexanes yielded 9.44 g of relatively pure product (Compound 6) (white crystals) in 70% yield; confirmed by HNMR.

Example 1.2.4

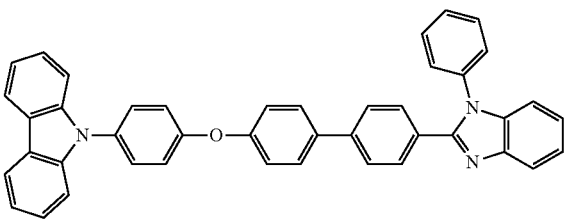

Compound 7

A mixture of Compound 6 (1.09 g, 3.40 mmol), Compound 5 (1.24 g, 3.42 mmol), cesium carbonate (2.23 g, 6.84 mmol), copper iodide (65 mg, 0.342 mmol), dimethylglycine hydrochloride (95 mg, 0.684 mmol) and anhydrous 1,4-dioxane (30 mL) was degassed for 30 minutes. The mixture was heated to 120° C. overnight under argon. After cooling, the resulting mixture was poured into DCM (250 mL) and filtered. The resulting filtrate was loaded onto silica gel. The resulting effluent from the flash column (silica, 5% to 50% ethyl acetate in hexanes gradient) gave an orange solid. Precipitation of the orange impurity was accomplished using DCM and methanol. The impurity was filtered off, and the filtrate containing the product was dried under vacuum. After drying, 270 mg of product (Compound 7) (pale orange powder, 13% yield) was isolated; pure by HNMR.

Example 1.3

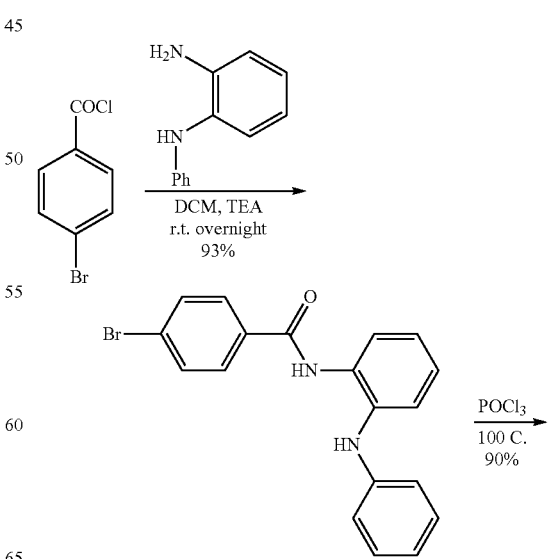

8

-continued

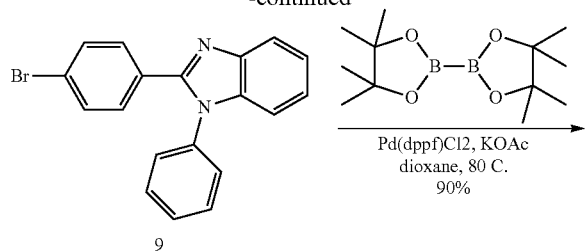

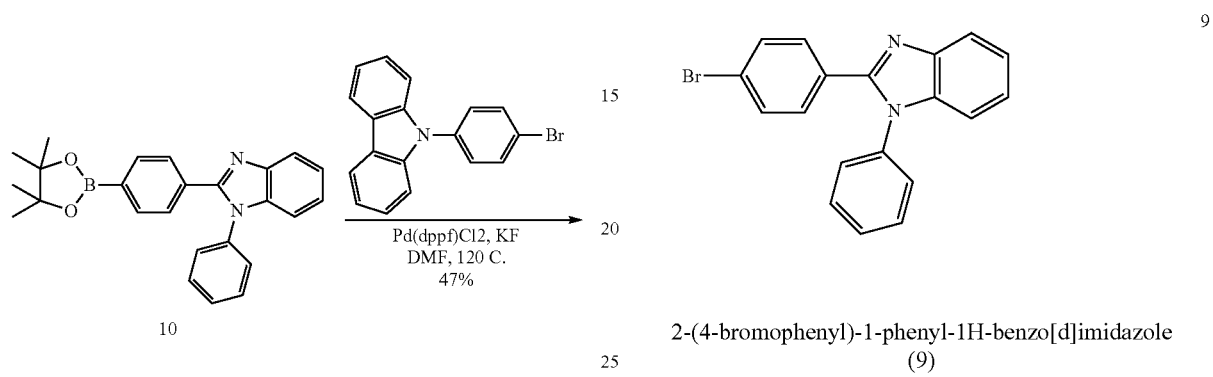

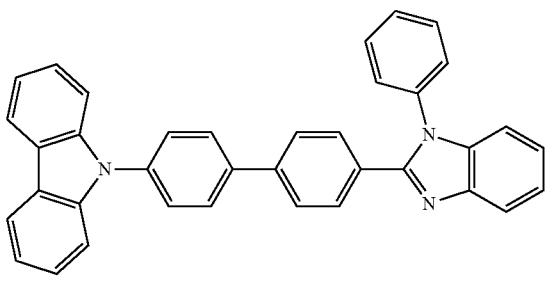

Example 1.3.1

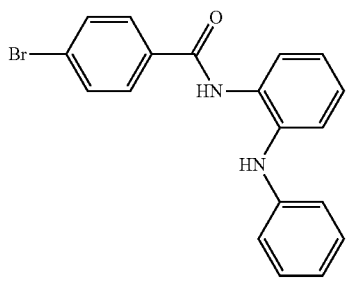

4-Bromo-N-(2-(phenylamino)phenyl)benzamide (8)

To a solution of 4-bromo-benzoyl chloride (11 g, 50 mmol) in anhydrous dichloromethane (DCM) (100 ml), was added N-phenylbenzene-1,2-diamine (10.2 g, 55 mmol), then triethylamine (17 ml, 122 mmol) slowly. The whole mixture was then stirred at room temperature (r.t.) overnight. Subsequent filtration gave a white solid (Compound 8) (6.5 g). The filtrate was worked up with water (300 ml), and then extracted with DCM (300 ml) three times. The resulting organic phase was collected and dried over MgSO$_4$, concentrated and recrystallized in DCM/hexanes to give another portion of white solid (Compound 8) (10.6 g). The total amount of product (Compound 8) was 17.1 g, in 93% yield.

Example 1.3.2

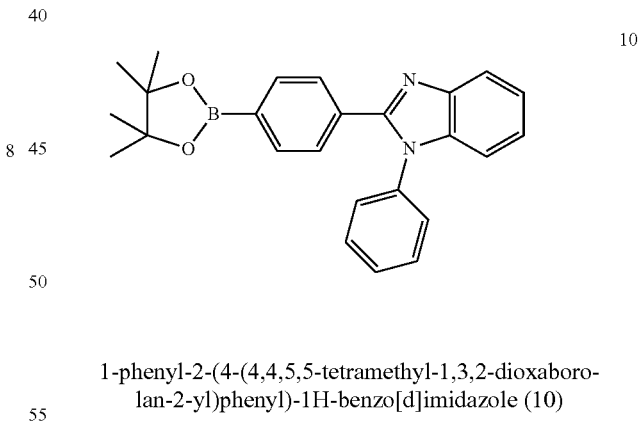

2-(4-bromophenyl)-1-phenyl-1H-benzo[d]imidazole (9)

To a suspension of amide 1 (9.6 g, 26 mmol) in anhydrous 1,4-dioxane (100 mL) was added phosphorous oxychloride (POCl$_3$) (9.2 mL, 100 mmol) slowly. The whole was then heated at 100° C. overnight. After cooling to r.t., the mixture was poured into ice (200 g) with stirring. Filtration, followed by recrystallization in DCM/hexanes gave a pale grey solid (Compound 9) (8.2 g, in 90% yield).

Example 1.3.3

1-phenyl-2-(4-(4,4,5,5-tetramethyl-1,3,2-dioxaborolan-2-yl)phenyl)-1H-benzo[d]imidazole (10)

A mixture of Compound 9 (0.70 g, 2 mmol), bis(pinacolate)diborane (0.533 g, 2.1 mmol), 1,1'-Bis(diphenylphosphino)ferrocene]dichloropalladium (Pd(dppf)Cl$_2$) (0.060 g, 0.08 mmol) and anhydrous potassium acetate (0.393 g, 4 mmol) in 1,4-dioxane (20 mL) was heated at 80° C. under argon overnight. After cooling to r.t., the whole mixture was diluted with ethyl acetate (80 mL) then filtered. The solution was absorbed on silica gel, then purified by column chromatography (hexanes/ethyl acetate 5:1 to 3:1) to give a white solid (Compound 10) (0.64 g, in 81% yield).

Example 1.3.4

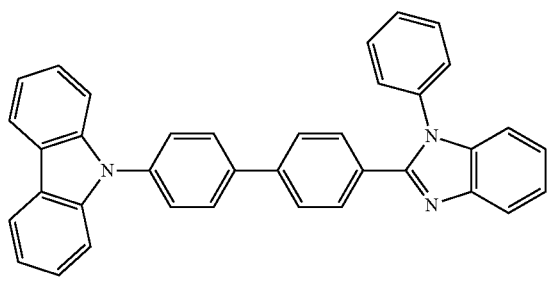

9-(4'-(1-phenyl-1H-benzo[d]imidazol-2-yl)biphenyl-4-yl)-9H-carbazole (11)

A mixture of Compound 10 (1.41 g, 3.56 mmol), 9-(4-bromophenyl)-9H-carbazole (1.15 g, 3.56 mmol), Pd(dppf)Cl2 (100 mg, 0.14 mmol) and KF (0.619 g, 10.7 mmol) in anhydrous DMF (20 mL) was heated at 120° C. under argon overnight. After cooling to r.t., ethyl acetate (200 mL) was added and the whole was stirred for 15 min. The resulting mixture was filtered. The solid was collected and dissolved in DCM (200 mL), which was filtered, concentrated and recrystallized to give a white solid (Compound 11) (550 mg).

The filtrate from the first separation was absorbed on silica gel, then purified by column chromatography (hexanes/ethyl acetate 7:1 to 3:1) to give a pale yellow solid (Compound 11) (300 mg). NMR shows both of the two solids are desired product (Compound 11), with total amount of 850 mg, in 47% yield.

Example 1.4

Overall Scheme:

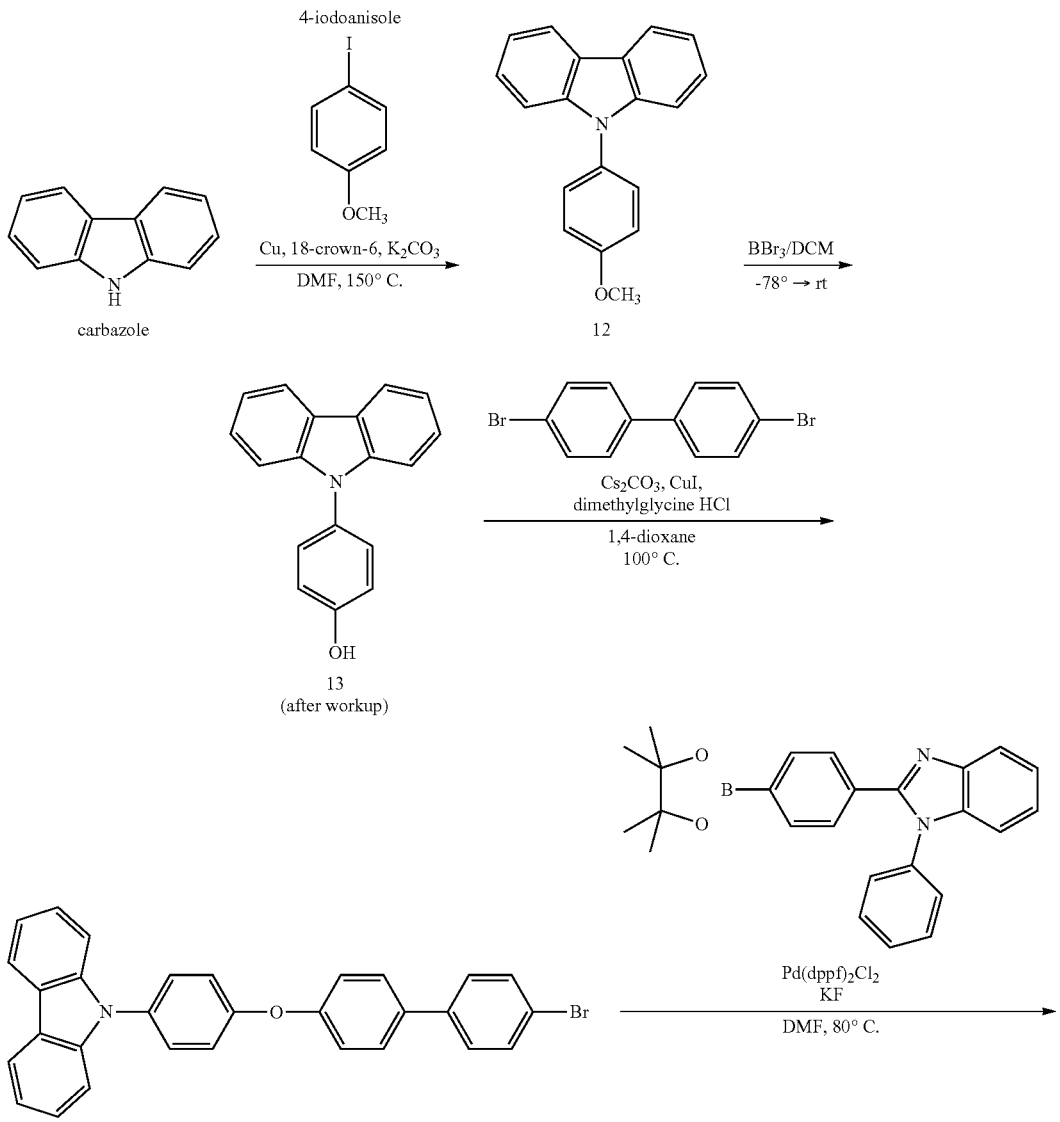

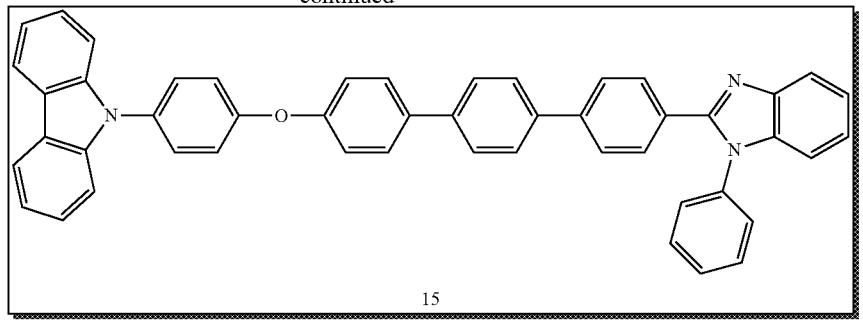

Example 1.4.1

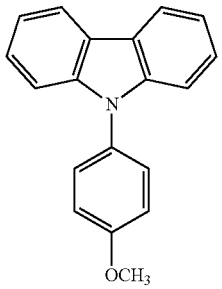

Compound 12

9-(4-methoxyphenyl)-9H-carbazole (Compound 12)

A mixture of carbazole (10.0 g, 60.2 mmol), 4-iodoanisole (21.1 g, 90.4 mmol), copper powder (28.58 g, 450 mmol), 18-crown-6 (9.33 g, 35.3 mmol), and potassium carbonate (62.1 g, 450 mmol) was degassed in dimethylformamide (anhydrous, 100 mL) for 45 minutes. The resulting mixture was heated to 150° C. overnight under argon. After cooling, the mixture was poured into DCM (500 mL). Then, the remaining copper and salts were filtered off. The resulting filtrate washed with water (2×200 mL). The organic layer was collected, dried over sodium sulfate, and then loaded onto silica gel. A flash column (gradient of 3-5% ethyl acetate in hexanes) and reprecipitation from DCM/hexanes gave 11.71 g (71% yield) of product (Compound 12); confirmed pure by HNMR.

Example 1.4.2

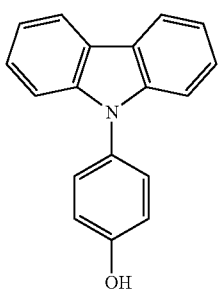

Compound 13

4-(9H-carbazol-9-yl)phenol (Compound 13)

Compound 12 (11.63 g, 42.6 mmol) was dissolved in DCM and the solution was cooled to −77° C. Boron tribromide (45 mL of a 1M solution) was added dropwise to the cold solution. The solution was stirred overnight under argon while slowly warming to room temperature. LCMS showed a single peak with desired mass (M⁻=528). Methanol (100 mL) was added to reaction mixture; and stirred for 30 minutes. The whole was loaded onto silica gel. A flash column (gradient of 10-20% ethyl acetate in hexanes) gave 10.94 g of product (Compound 13) (99% yield), confirmed pure by HNMR.

Example 1.4.3

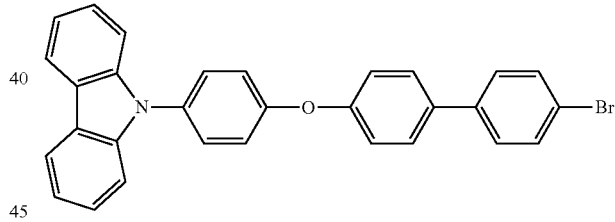

Compound 14

9-(4-(4'-bromobiphenyl-4-yloxy)phenyl)-9H-carbazole (Compound 14)

A mixture of the Compound 13 (10.0 g, 8.3 mmol), 4,4'-dibromobiphenyl (24.1 g, 77.2 mmol), cesium carbonate (25.2 g, 77.2 mmol), copper iodide (700 mg, 3.86 mmol), and dimethylglycine hydrochloride (1.62 g, 11.6 mmol) was degassed in 1,4-dioxane (anhydrous, 100 mL) for 45 minutes. The mixture was heated to 120° C. overnight under argon. After cooling, the mixture was poured into DCM (300 mL) the subsequent mixture was washed with water and brine. The organic layer was collected, dried over sodium sulfate, and loaded onto silica gel. A plug using 10% ethyl acetate in hexanes was used to remove baseline impurities. A subsequent flash column (5% toluene in hexanes), and precipitation from DCM/methanol gave 11.17 g of product (Compound 14) (59% yield), confirmed pure by HNMR.

Example 1.4.4

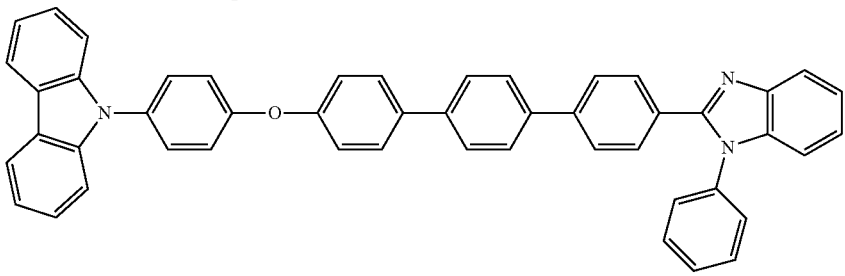

Compound 15

A mixture of the Compound 14 (1.85 g, 3.79 mmol), 1-phenyl-2-(4-(4,4,5,5-tetramethyl-1,3,2-dioxaborolan-2-yl)phenyl)-1H-benzo[d]imidazole (1.5 g, 3.79 mmol), 1,1'-Bis(diphenylphosphino)ferrocene]dichloropalladium (139 mg, 0.190 mmol), and potassium fluoride (661 mg, 11.4 mmol) was degassed in dimethylformamide (anhydrous, 30 mL) for 30 minutes. The mixture was heated to 80° C. overnight under argon. After cooling, the mixture was poured into DCM (200 mL) and washed with water and brine. The organic layer was collected, dried over sodium sulfate, and loaded onto silica gel. A flash column (20% ethyl acetate in hexanes) and recrystallization from DCM/methanol gave 1.83 g (71% yield) of product (Compound 15); confirmed pure by HNMR.

Example 1.5

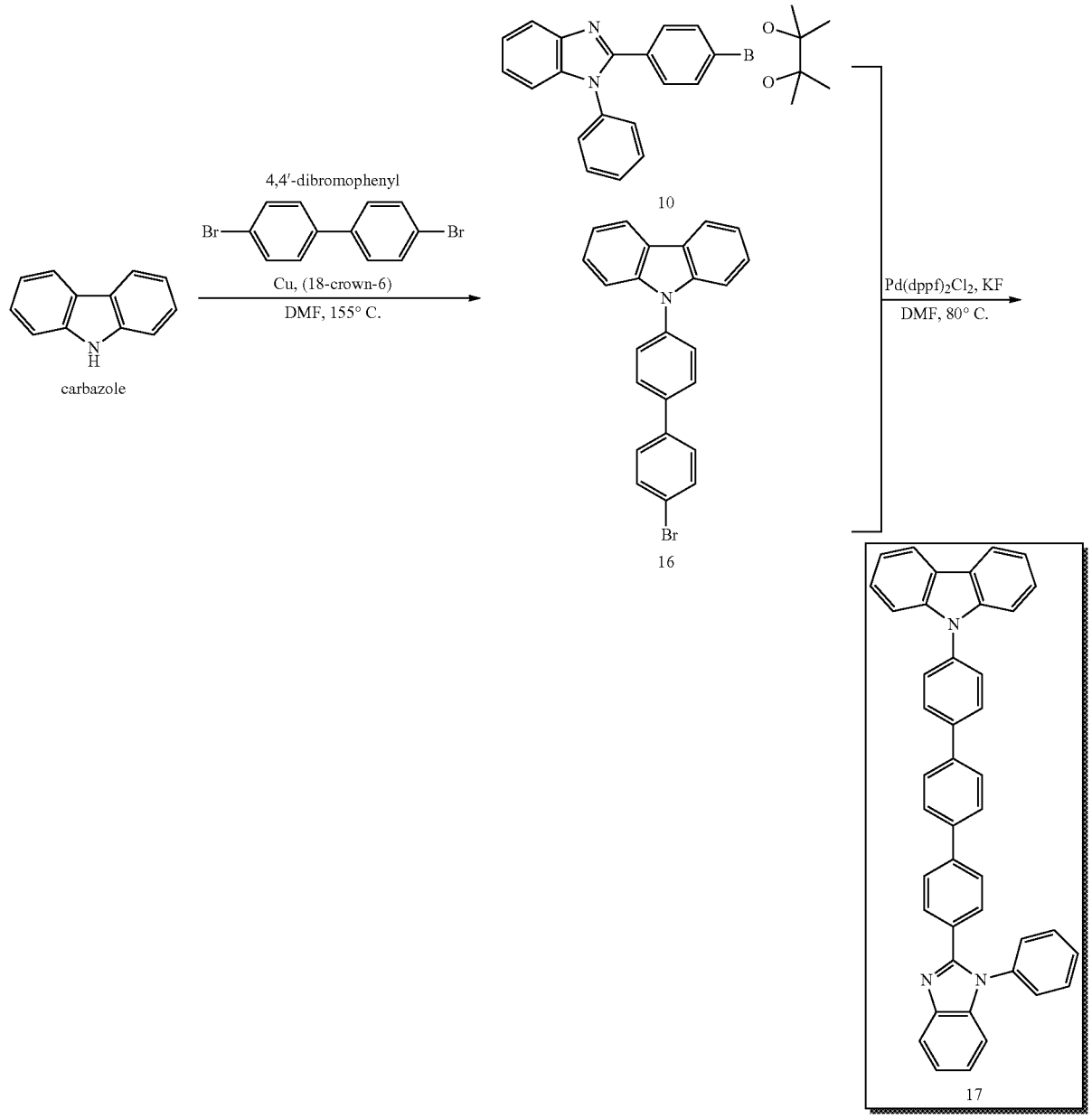

Example 1.5.1

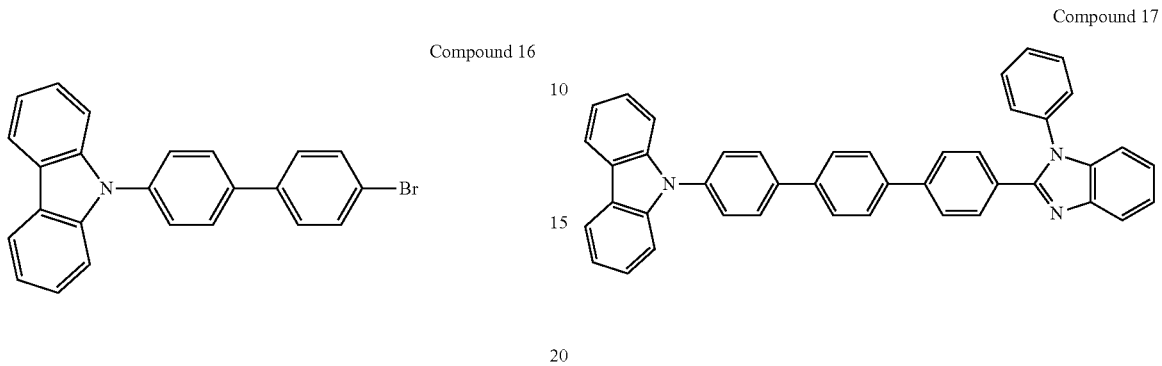

Compound 16

9-(4'-bromobiphenyl-4-yl)-9H-carbazole

A mixture of carbazole (300 mg, 1.81 mmol), 4,4'-dibromobiphenyl (846 mg, 2.71 mmol), copper (344 mg, 5.43 mmol), 18-crown-6 (187 mg, 0.71 mmol), potassium carbonate (750 mg, 5.43 mmol), and anhydrous N,N-dimethylformamide (10 mL) was degassed for 30 minutes. The mixture was heated to 155° C. for 66 hours under argon. After cooling, the mixture was poured into DCM (400 mL) and the subsequent mixture was filtered. The filtrate was loaded on silica gel. A flash column (silica, 10% DCM in hexane) and reprecipitation in DCM/hexanes yielded 304 mg (42% yield) of pure product; confirmed by HNMR.

Example 1.5.2

Compound 17

A mixture of Compound 16 (250 mg, 0.63 mmol), 1-phenyl-2-(4-(4,4,5,5-tetramethyl-1,3,2-dioxaborolan-2-yl)phenyl)-1H-benzo[d]imidazole (Compound 10) (250 mg, 0.63 mmol), [1,1'-Bis(diphenylphosphino)ferrocene]dichloropalladium(II) (23 mg, 0.03 mmol), potassium fluoride (110 mg, 1.89 mmol), and dimethylformamide (anhydrous, 15 mL) was degassed for 20 minutes. The mixture was then heated to 80° C. overnight under argon. After cooling, the mixture was poured into DCM (200 mL), and solids were filtered off. The resulting filtrate was washed with water (2×100 mL), dried over sodium sulfate, and then loaded onto silica gel. A flash column (gradient of 3-10% ethyl acetate in DCM) and recrystallization using DCM/hexanes gave 170 mg (46% yield) of material (Compound 17); confirmed pure by HNMR.

Example 1.6

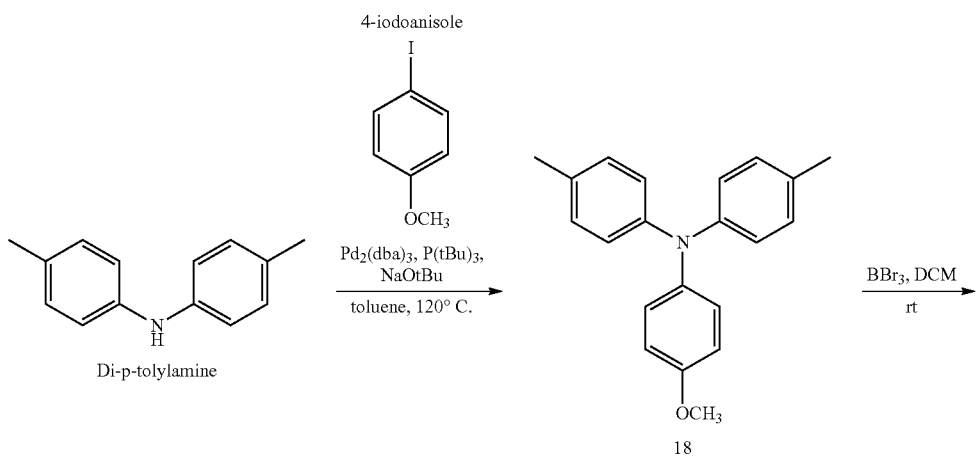

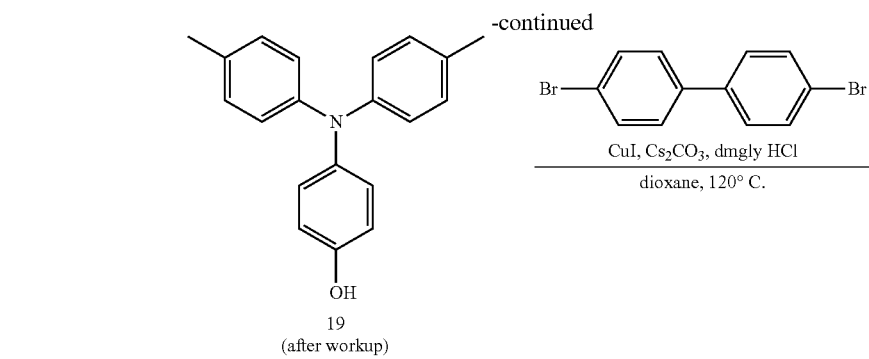

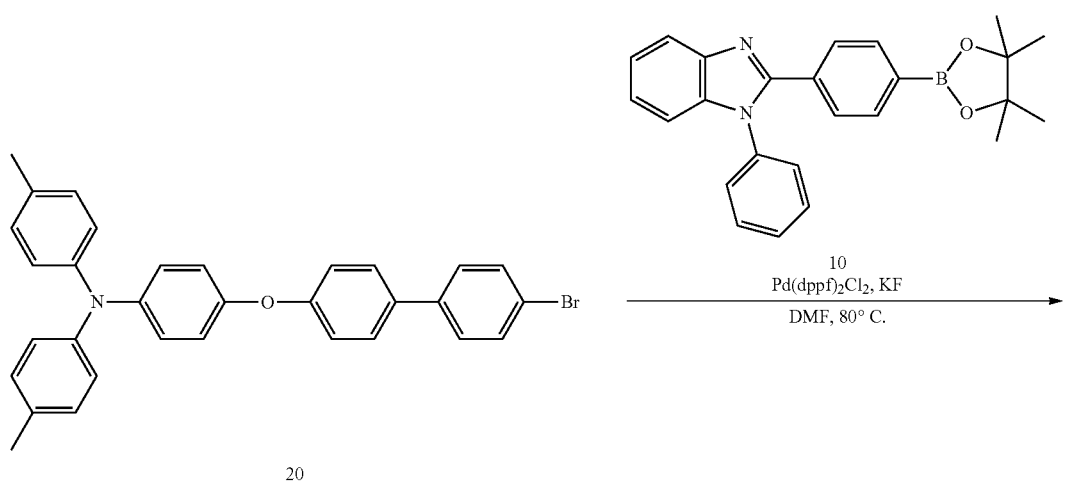

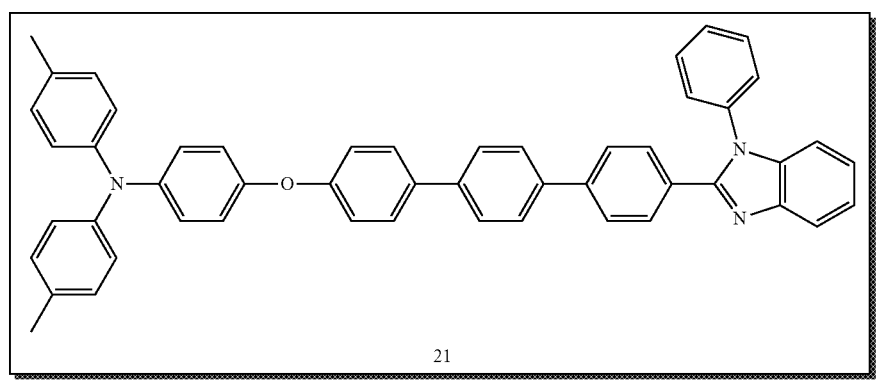

Example 1.6.1

4-Methoxy-N,N-di-p-tolylaniline (Compound 18)

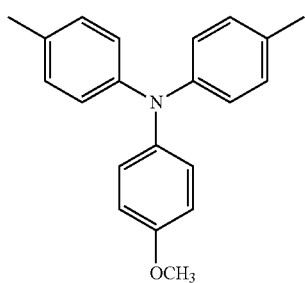

Compound 18

A mixture of tris(dibenzylideneacetone)dipalladium (60 mg, catalytic), and tri-tert-butyl phosphine (5 ml of a 10% solution in hexanes) was degassed in toluene (anhydrous, 60 mL) for 20 minutes. Di-p-tolylamine (4.0 g, 20.3 mmol), and 4-iodoanisole (11.88 g, 50.8 mmol) were added and degassing continued 15 minutes. Sodium tert-butoxide (2.4 g, 25 mmol) was added, and mixture was further degassed for 10 minutes. The whole mixture was heated overnight at 120° C. under argon. After cooling, the mixture was poured into ethyl acetate and washed with water (2×200 mL). The organic layer was collected and dried over sodium sulfate, then loaded onto silica gel. A flash column (gradient of 2-3% ethyl acetate in hexanes) gave 3.26 g of material (Compound 18) (53% yield); confirmed pure by HNMR.

Example 1.6.2

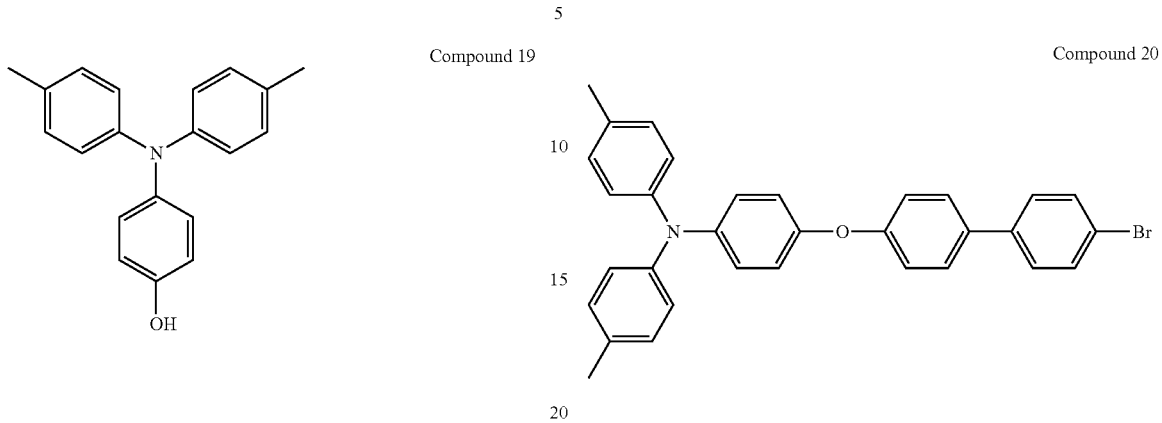

Compound 19

4-(di-p-tolylamino)phenol (Compound 19)

Compound 18 (3.05 g, 10.1 mmol) was dissolved in DCM (anhydrous, 50 mL) and the solution was cooled to −77° C. Boron tribromide (12 mL of a 1 M solution) was added dropwise to the cold solution. The whole mixture was stirred and slowly warmed to room temperature overnight under argon. LCMS showed a single desired mass of 288 (M⁻). The mixture was poured into methanol (200 mL) and stirred for 45 minutes. The mixture was then concentrated under vacuum, then DCM (100 mL) was added. The solution was washed with water (2×200 mL). The organic layer was collected, dried over sodium sulfate, and concentrated under vacuum. Precipitation of the organic layer using hexanes gave 2.44 g of material (Compound 19) (84% yield); confirmed pure by HNMR.

Example 1.6.3

Compound 20

4-(4'-bromobiphenyl-4-yloxy)-N,N-di-p-tolylaniline (Compound 20)

A mixture of the Compound 19 (2.4 g, 8.3 mmol), 4,4'-dibromobiphenyl (1.25 g, 4.0 mmol), cesium carbonate (5.41 g, 16.6 mmol), copper iodide (158 mg, 0.83 mmol), and dimethylglycine hydrochloride (348 mg, 2.49 mmol) was degassed in 1,4-dioxane (anhydrous, 40 mL) for 45 minutes. The mixture was heated to 120° C. overnight under argon. After cooling, the mixture was poured into DCM (300 mL), and the subsequent mixture was washed with water and brine. The organic layer was collected, dried over sodium sulfate, and loaded onto silica gel. A flash column (gradient of 5-20% DCM in hexanes), and reprecipitation from DCM/hexanes gave 760 mg of product (Compound 20) (37% yield), confirmed pure by HNMR.

Example 1.6.4

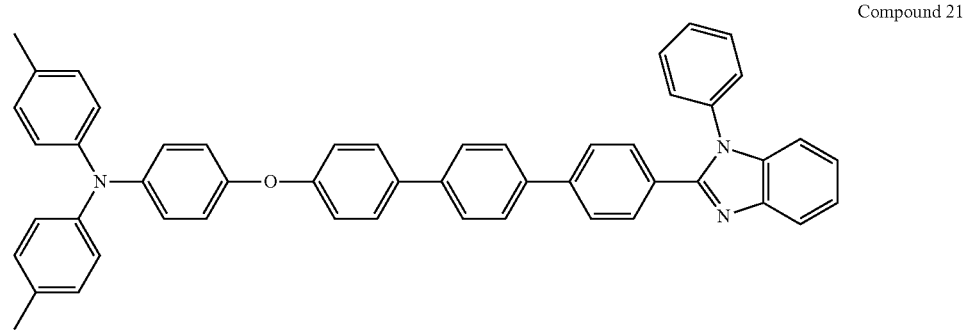 [SMILES: Cc1ccc(N(c2ccc(C)cc2)c2ccc(Oc3ccc(-c4ccc(-c5ccc(-c6nc7ccccc7n6-c6ccccc6)cc5)cc4)cc3)cc2)cc1]

Compound 21

A mixture of Compound 20 (656 mg, 1.26 mmol), 1-phenyl-2-(4-(4,4,5,5-tetramethyl-1,3,2-dioxaborolan-2-yl)phenyl)-1H-benzo[d]imidazole (500 mg, 1.26 mmol), 1,1'-Bis(diphenylphosphino)ferrocene]dichloropalladium (100 mg, catalytic), and potassium fluoride (220 mg, 3.8 mmol) was degassed in dimethylformamide (anhydrous, 8 mL) for 30 minutes. Mixture was heated to 80° C. overnight under argon. After cooling, the mixture was poured into water (200 mL). Product was extracted with DCM (2×150 mL). The organic layer collected, dried over sodium sulfate, and loaded onto silica gel. A flash column (gradient of 15-45% ethyl acetate in hexanes) and reprecipitation from DCM/methanol gave 400 mg (45% yield) of product; confirmed pure by HNMR.

Example 1.7

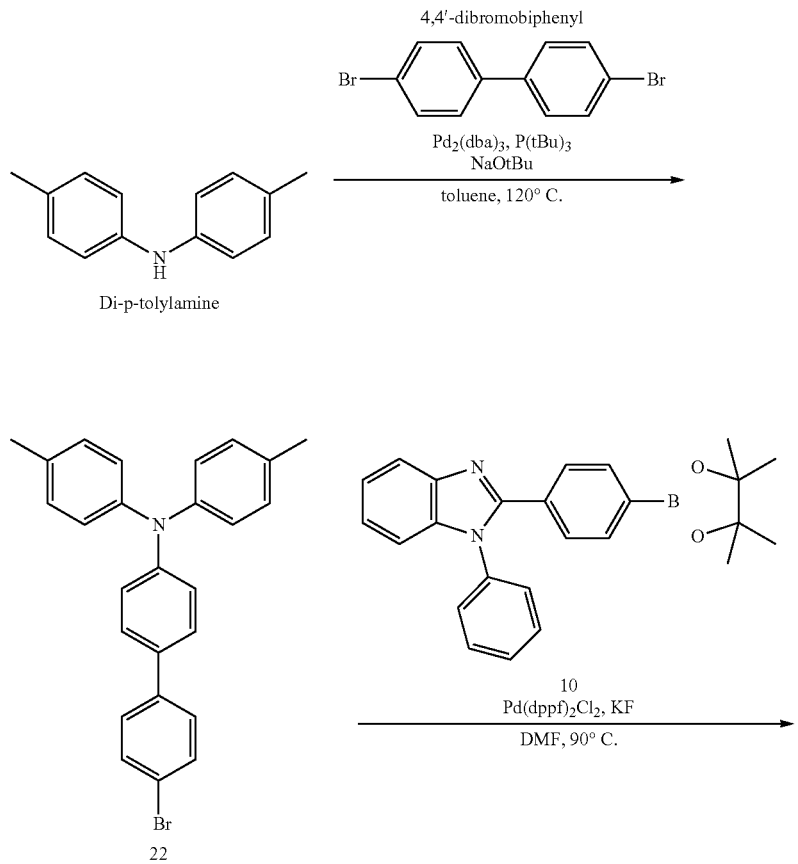

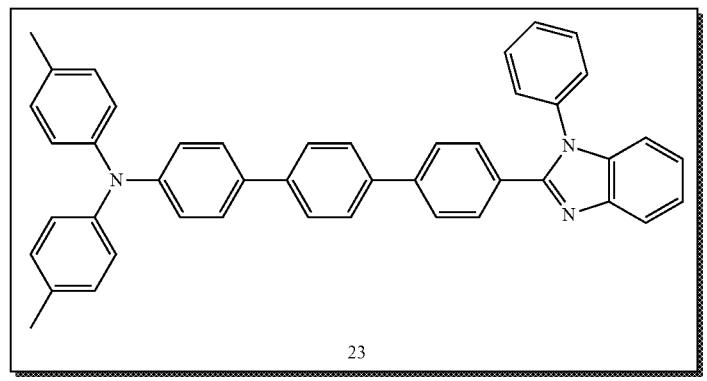

Example 1.7.1

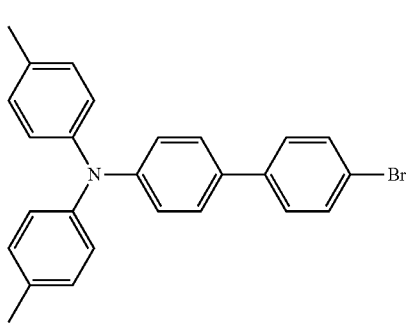

Compound 22

4'-bromo-N,N-di-p-tolylbiphenyl-4-amine
(Compound 22)

A mixture of tris(dibenzylideneacetone)dipalladium (353 mg, 0.385 mmol), and tri-tert-butyl phosphine (3.11 g of a 10% solution in hexanes) was degassed in toluene (anhydrous, 50 mL) for 20 minutes. Di-p-tolylamine (3.00 g, 15.2 mmol), and 4,4'-dibromobiphenyl (4.80 g, 15.4 mmol) were added and the mixture was further degassed for 15 minutes. Sodium tert-butoxide (2.4 g, 25 mmol) was added, and mixture was further degassed for 10 minutes. The whole was heated overnight at 120° C. under argon. After cooling, the mixture was poured into DCM, and solids were filtered off. Filtrate was washed with water and brine. The organic layer was collected and dried over sodium sulfate, then loaded onto silica gel. A flash column (gradient of 2-20% ethyl acetate in hexanes) gave 190 mg of material (3% yield); confirmed pure by HNMR.

Example 1.7.2

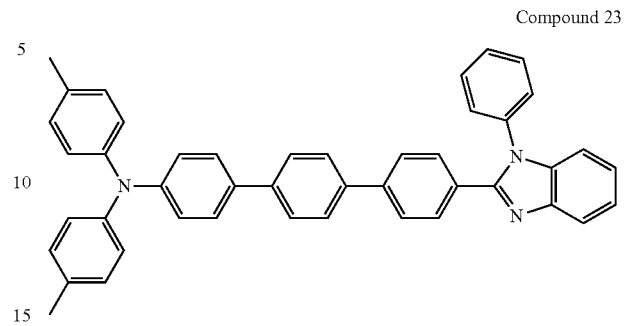

Compound 23

A mixture of Compound 22 (170 mg, 0.397 mmol), 1-phenyl-2-(4-(4,4,5,5-tetramethyl-1,3,2-dioxaborolan-2-yl)phenyl)-1H-benzo[d]imidazole (173 mg, 0.436 mmol), 1,1'-Bis(diphenylphosphino)ferrocene]dichloropalladium (15 mg, 0.02 mmol), and potassium fluoride (70 mg, 1.2 mmol) was degassed in dimethylformamide (anhydrous, 15 mL) for 30 minutes. Mixture was heated to 90° C. overnight under argon. After cooling, the mixture was poured into water and filtered. The solids were dissolved in DCM (50 mL) and solution was washed with water and brine. To filtrate from first filtration: filtrate was extracted with DCM (2×100 mL). All organic phases were combined, dried over sodium sulfate, and loaded onto silica gel. A flash column (gradient of 10-20% ethyl acetate in hexanes) and reprecipitation in DCM/methanol gave 146 mg (59% yield) of product (Compound 23); confirmed by HNMR.

Example 1.8.1

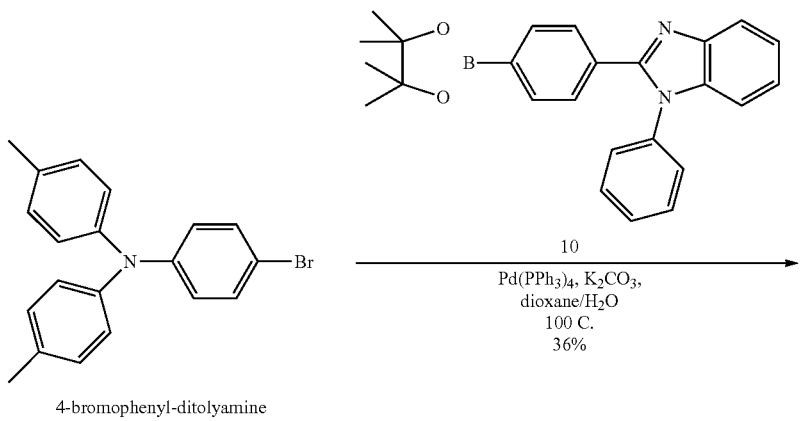

4-bromophenyl-ditolyamine

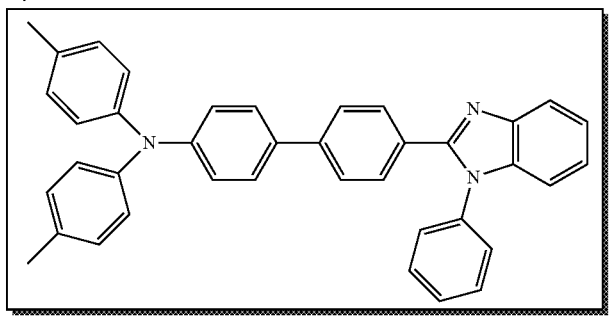

24

Compound 24

A mixture of 4-bromophenyl-ditolyamine (2.80 g, 8.0 mmol), Compound 10 (3.15 g, 8.0 mmol), Pd(PPh$_3$)$_4$ (0.90 g, 0.8 mmol) and K$_2$CO$_3$ (2.76 g, 20 mmol) in 1,4-dioxane/H$_2$O (30 mL/5 mL) was degassed and the resulting mixture was heated at about 100° C. overnight. After cooling to room temperature, the resulting mixture was worked up with 10% NaCl aqueous solution, then extracted with ethyl acetate (150 mL×2). The organic phase was collected and dried over Na$_2$SO$_4$, then absorbed on silica gel and purified by flash chromatography (hexanes/ethyl acetate 6:1 to 4:1) to give a yellow solid, which was recrystallized in dichloromethane/methanol 3 times to afford a white solid (Compound 24) (1.55 g, 36% yield).

Example 1.9.1

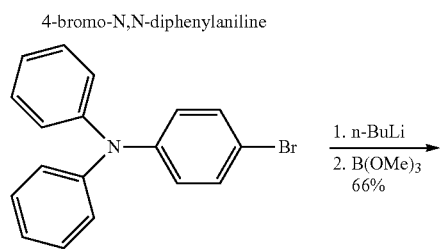

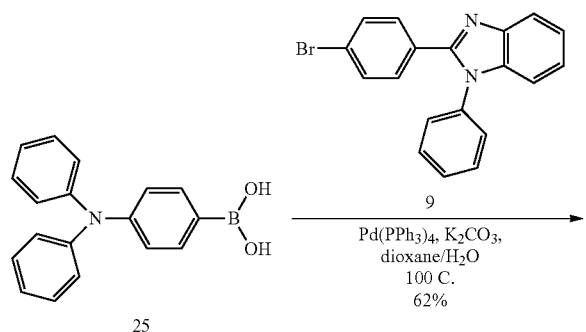

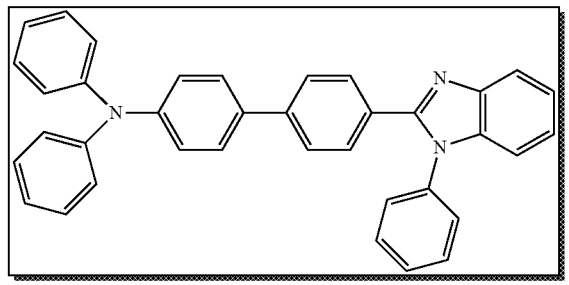

26

(4-(diphenylamino)phenyl)boronic acid (Compound 25)

To a solution of 4-bromo-N,N-diphenylaniline (22 g, 68 mmol) in anhydrous THF (170 mL) was added n-BuLi solution (2.5 M in hexanes, 20 mL, 75 mmol) at −78° C. slowly. The resulting mixture was then stirred at −78° C. for about 5 hours, then freshly distilled trimethylborate (8.8 mL, 80 mmol) was added. The resulting mixture was stirred at room temperature over weekend. To the solution, 5% HCl solution (150 mL) was added and stirred overnight, then extracted with ethyl acetate (200 mL×2). The organic phase was collected and dried over Na$_2$SO$_4$. After removal of solvent, the remaining solid was recrystallized in dichloromethane/hexanes to give a white solid (11.0 g). The filtrate solution was purified by flash chromatography (silica gel, hexnaes/ethyl acetate, 9:1 to 2:1) to give additional white solid (2.0 g). The total amount of product (Compound 25) was 13 gram, in 66% yield.

Compound 26

A mixture of Compound 25 (4-(diphenylamino)phenyl)boronic acid (900 mg, 3.1 mmol), Compound 9 (1.09 g, 3.1 mmol), Pd(PPh$_3$)$_4$ (180 mg, 0.16 mmol) and K$_2$CO$_3$ (1.38 g, 10 mmol) in 1,4-dioxane/H$_2$O (25 mL/5 mL) was degassed and the resulting mixture was heated at about 100° C. overnight under an argon atmosphere. After cooling to room temperature, the resulting mixture was poured into water, extracted with ethyl acetate (100 mL×2). The organic phase was dried over Na$_2$SO$_4$ and filtered. After addition of hexanes (100 mL), a yellow precipitate formed after about one hour. Filtration gave a yellow solid (760 mg) and the filtrate was absorbed on silica gel and purified by flash chromatography to give a yellow solid (200 mg). The total amount of product (Compound 26) was 960 mg in 62% yield.

Example 1.10.1
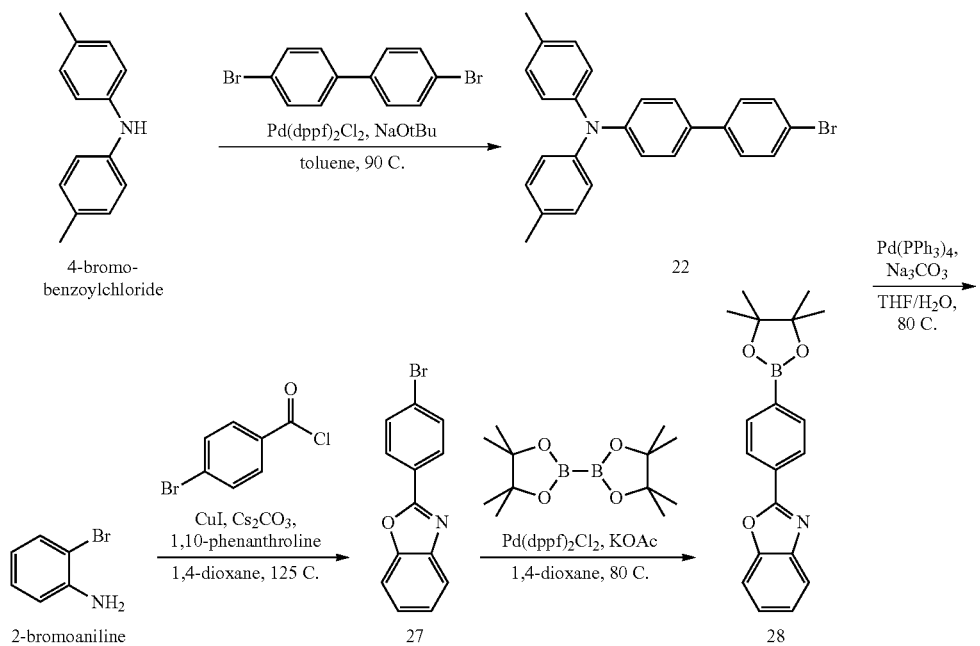
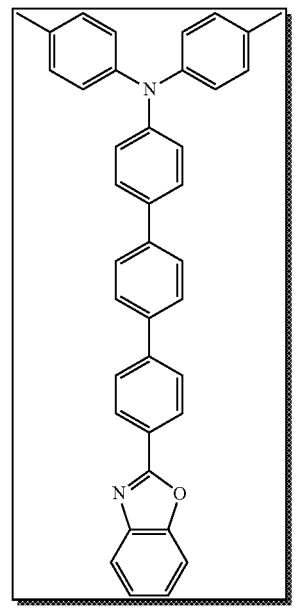
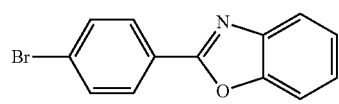

2-(4-bromophenyl)benzo[d]oxazole (Compound 27): A mixture of 4-bromobenzoylchloride (4.84 g, 22 mmol), 2-bromoaniline (3.8 g, 22 mmol), CuI (0.21 g, 1.1 mmol), Cs$_2$CO$_3$ (14.3 g, 44 mmol) and 1,10-phenathroline (0.398 g, 2.2 mmol) in anhydrous 1,4-dioxane (80 mL) was degassed and the resulting mixture was heated at about 125° C. under argon overnight. The resulting mixture was cooled and poured into ethyl acetate (~200 mL) and filtered. The filtrate was absorbed on silica gel, purified by column chromatography (hexanes/ethyl acetate 4:1), and precipitated by hexanes to give a white solid (Compound 27) (5.2 g, in 87% yield).

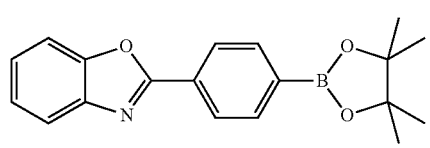

2-(4-(4,4,5,5-tetramethyl-1,3,2-dioxaborolan-2-yl)phenyl)benzo[d]oxazole (Compound 28)

A mixture of 10 (4.45 g, 16 mmol), bis(pinacolate)diborane (4.09 g, 16.1 mmol), anhydrous potassium acetate (3.14 g, 32 mmol) and Pd(dppf)Cl$_2$ (0.48 g, 0.66 mmol) in anhydrous 1,4-dioxane (80 mL) was degassed and the resulting mixture was heated at about 85° C. for about 48 hours under argon. After cooling to room temperature, the mixture was poured into ethyl acetate (~200 mL) and filtered. The filtrate was absorbed on silica gel and purified by column chromatography (hexanes/ethyl acetate, 4:1) to give a white solid (Compound 28) (4.15 g, in 81% yield).

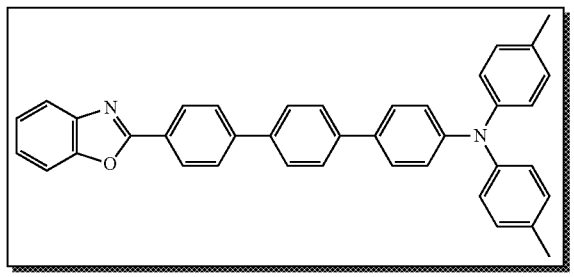

Compound 29

A mixture of Compound 28 (0.66 g, 2.05 mmol), Compound 22 (0.80 g, 1.87 mmol), Na$_2$CO$_3$ (0.708 g, 6.68 mmol) and Pd(PPh$_3$)$_4$ (0.065 g, 56.1 mmol) in THF/H$_2$O (10 mL/6 mL) was degassed and the resulting mixture was heated at about 80° C. overnight under argon atmosphere. After cooling, the resulting mixture was poured into dichloromethane (100 mL) and washed with water (2×200 mL) and brine (100 mL). The organic phase was collected, dried over Na$_2$SO$_4$, then purified by flash chromatography (silica gel, hexanes/ethyl acetate 40:1 to 9:1) to give a solid (Compound 29) (0.936 g, in 93% yield).

Example 1.11.1

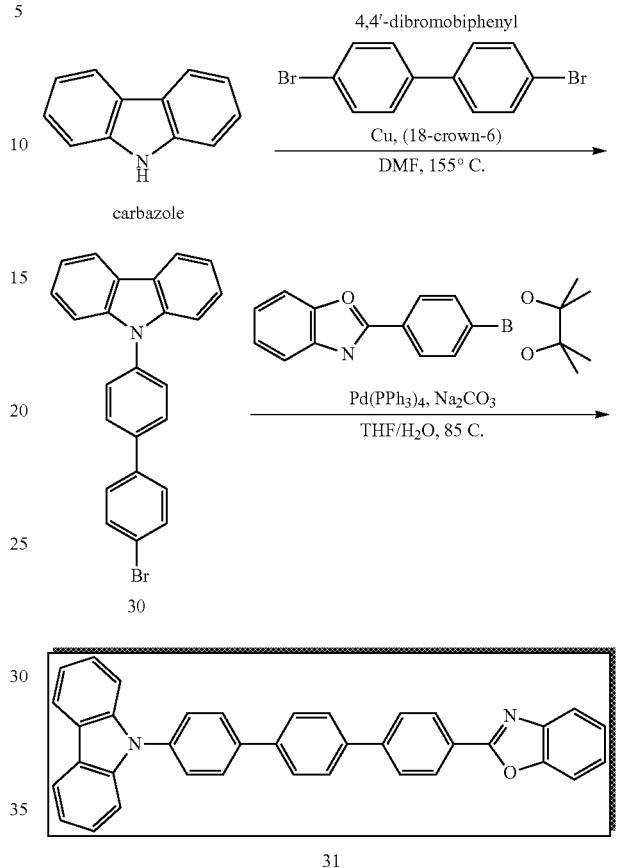

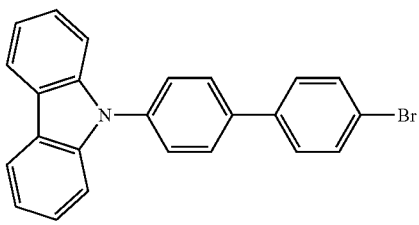

9-(4'-bromobiphenyl-4-yl)-9H-carbazole (Compound 30)

A mixture of carbazole (300 mg, 1.81 mmol), 4,4'-dibromobiphenyl (846 mg, 2.71 mmol), copper (344 mg, 5.43 mmol), 18-crown-6 (187 mg, 0.71 mmol), potassium carbonate (750 mg, 5.43 mmol), and anhydrous N,N-dimethylformamide (10 mL) was degassed for 30 minutes. The resulting mixture was then heated to about 155° C. for 66 hours under argon. After cooling, the resulting mixture was poured into methylene chloride (400 mL) and the subsequent mixture was filtered. The filtrate was loaded on silica gel. A flash column (silica, 10% methylene chloride in hexane) and reprecipitation in methylene chloride/hexanes yielded 304 mg (42% yield) of pure product; confirmed by HNMR.

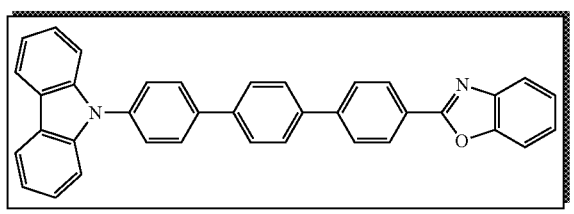

Compound 31

A mixture of 9-(4'-bromobiphenyl-4-yl)-9H-carbazole (Compound 30) (1.6 g, 4.03 mmol), Compound 28 (1.42 g, 4.43 mmol), Na$_2$CO$_3$ (1.53 g, 14.39 mmol) and Pd(PPh$_3$)$_4$ (0.14 g, 0.121 mmol) in THF/H$_2$O (24 mL/14 mL) was degassed and the resulting mixture was heated to about 85° C. overnight under argon atmosphere. After cooling, the resulting mixture was poured into dichloromethane (200 mL), and washed with water (2×150 mL) and brine (150 mL). The organic phase was collected and dried over Na$_2$SO$_4$, and concentrated to form a grey precipitate. Filtration gave a filtrate (A) and solid, which was redissolved in chloroform (550 mL) and filter off suspended particles, the clear filtrate (B) was kept at −15 C.° overnight to form a white solid (1.19 g). The filtrate (C) was combined with the Filtrate A and absorbed on silica gel, purified by flash chromatography (dichloromethane) give an additional 0.52 g solid. Both solids were combined and washed with hot ethyl acetate, and filtered to yield the product (Compound 31)(1.66 g, 81% yield).

Example 1.12.1

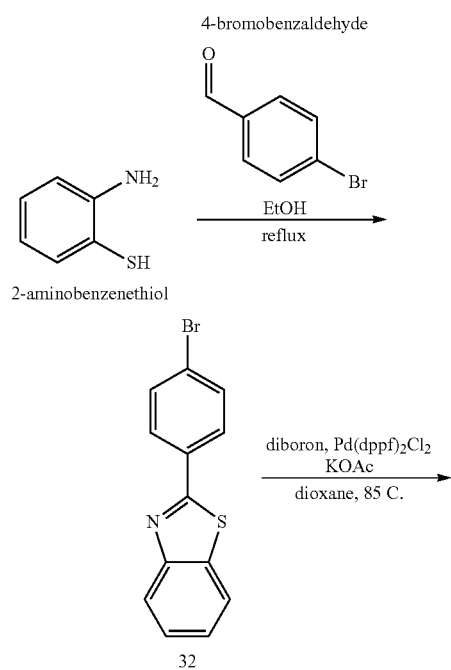

2-(4-bromophenyl)benzo[d]thioxazole (32)

A mixture of 2-aminobenzenethiol (2.0 g, 15.97 mmol), 4-bromobenzaldehyde (2.95 g, 15.97 mmol) and 50 mg of 10% Pd on carbon in ethanol (50 mL) was bubbled with air for about 20 min and then heated to reflux for about 6 days. After cooling, the mixture was poured into dichloromethane (100 mL), the catalyst was filtered off. The filtrated was washed with water (100 mL) and brine (100 mL), then dried over Na$_2$SO$_4$, followed by flash chromatography (silica gel, hexanes/ethyl acetate 20:1) and recrystallized in dichloromethane/methanol to give a white solid (Compound 32) (2.90 g, in 63% yield).

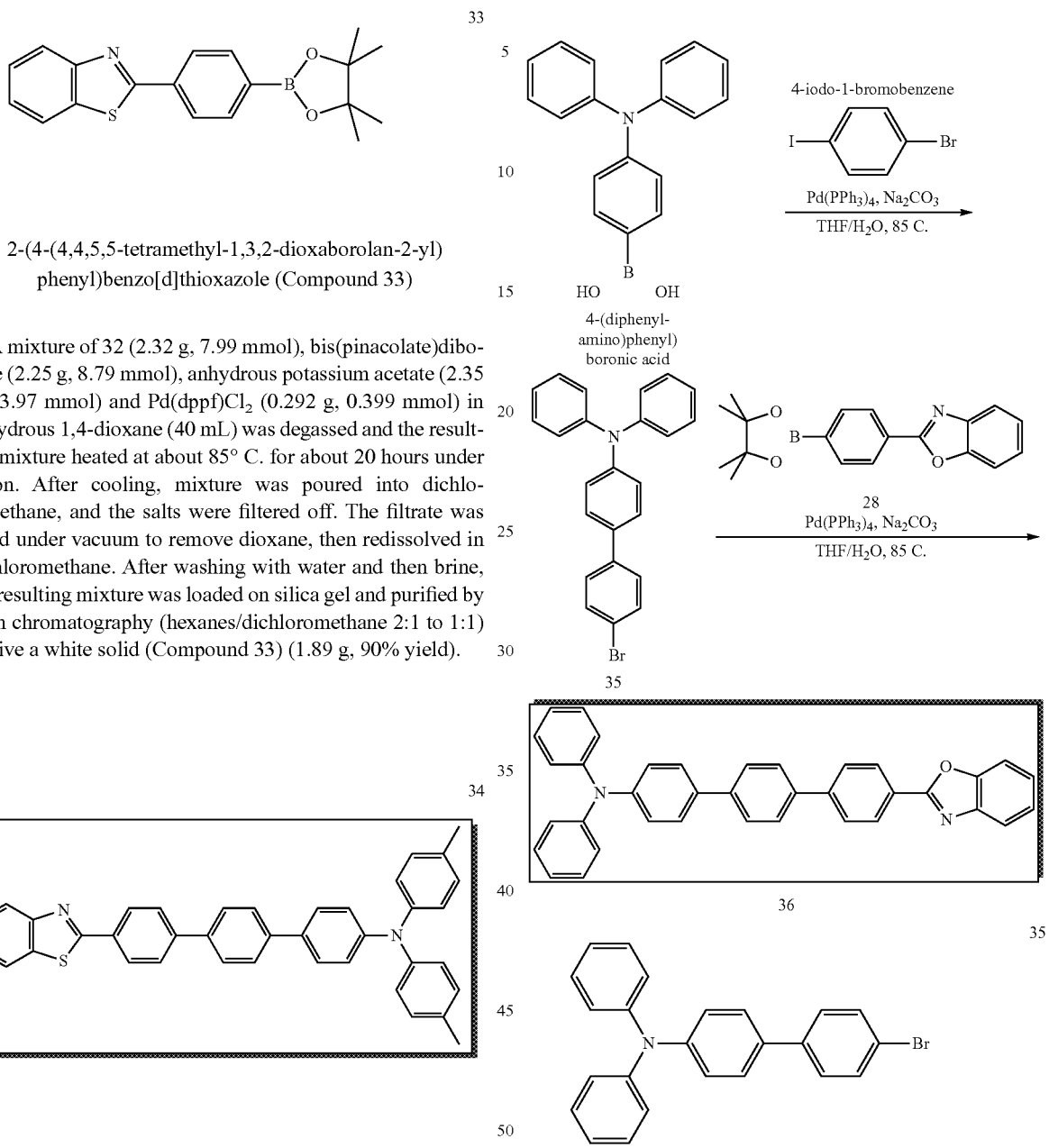

2-(4-(4,4,5,5-tetramethyl-1,3,2-dioxaborolan-2-yl)phenyl)benzo[d]thioxazole (Compound 33)

A mixture of 32 (2.32 g, 7.99 mmol), bis(pinacolate)diborane (2.25 g, 8.79 mmol), anhydrous potassium acetate (2.35 g, 23.97 mmol) and Pd(dppf)Cl$_2$ (0.292 g, 0.399 mmol) in anhydrous 1,4-dioxane (40 mL) was degassed and the resulting mixture heated at about 85° C. for about 20 hours under argon. After cooling, mixture was poured into dichloromethane, and the salts were filtered off. The filtrate was dried under vacuum to remove dioxane, then redissolved in dichloromethane. After washing with water and then brine, the resulting mixture was loaded on silica gel and purified by flash chromatography (hexanes/dichloromethane 2:1 to 1:1) to give a white solid (Compound 33) (1.89 g, 90% yield).

Compound 34

A mixture of 33 (1.48 g, 4.39 mmol), Compound 22 (1.71 g, 4.0 mmol), Na$_2$CO$_3$ (1.51 g, 14.28 mmol) and Pd(PPh$_3$)$_4$ (0.139 g, 0.12 mmol) in THF/water (24 mL/14 mL) was degassed for 45 min, then the resulting mixture was heated to reflux overnight under argon atmosphere. After cooling, the resulting mixture was poured into chloroform (300 mL) and heated to dissolve the product. The solution was washed with water (2×200 mL) and brine (200 mL). The organic phased was dried over Na$_2$SO$_4$ and concentrated to precipitate out solid, which was filtered and washed with methanol to give a solid (Compound 34) (1.24 g, 53% yield).

Example 1.13.1

4'-bromo-N,N-diphenyl-[1,1'-biphenyl]-4-amine (35)

A mixture of (4-(diphenylamino)phenyl)boronic acid (1.5 g, 5.19 mmol), 4-iodo-1-bromobenzene (1.33 g, 4.71 mmol), Na$_2$CO$_3$ (1.78 g, 16.8 mmol) and Pd(PPh$_3$)$_4$ (0.163 g, 0.141 mmol) in THF/H$_2$O (28 mL/17 mL) was degassed and the resulting mixture was heated at reflux overnight under an argon atmosphere. After cooling, the mixture was poured into dichloromethane (150 mL), then washed with water (2×150 mL) and brine (100 mL). The organic phase was dried over Na$_2$SO$_4$, purified with flash column chromatography (silica gel, hexanes/ethyl acetate 50:1) then recrystallized in dichloromethane/methanol to afford a white solid (Compound 35) (1.64 g, in 87% yield).

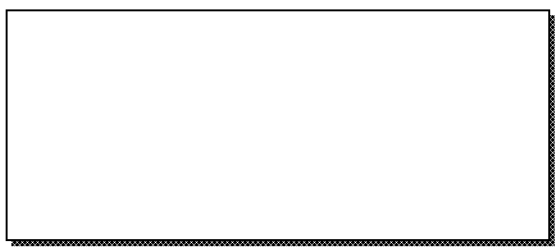

Compound 36

A mixture of 35 (1.40 g, 3.5 mmol), Compound 28 (1.52 g, 3.85 mmol), Na$_2$CO$_3$ (1.32 g, 12.5 mmol) and Pd(PPh$_3$)$_4$ (121 mg, 0.105 mmol) in THF/H$_2$O (21 mL/12.5 mL) was degassed and the resulting mixture was heated at reflux overnight under argon atmosphere. After cooling to room temperature, the resulting mixture was poured into dichloromethane (150 mL), then washed with water (150 mL) and brine (150 mL). The organic phase was dried over Na$_2$SO$_4$, absorbed on silica gel, and purified with flash column chromatography (hexane/ethyl acetate 5:1 to 2:1, then dichoromethane as eluent). The product was collected and recrystallized from acetone/hexanes to give a solid (1.69 g). It was recrystallized again in dichoromethane/ethyl acetate to give a solid (Compound 36) (1.4 g, 68% yield).

Example 2

OLED Device Configuration and Performance

Example 2.1

Fabrication of light-emitting device: the ITO coated glass substrates were cleaned by ultrasound in acetone, and consecutively in 2-propanol, baked at 110° C. for 3 hours, followed by treatment with oxygen plasma for 5 min. A layer of PEDOT: PSS (Baytron P purchased from H.C. Starck) was spin-coated at 3000 rpm onto the pre-cleaned and O$_2$-plasma treated (ITO)-substrate and annealed at 180° C. for 10 min, yielding a thickness of around 40 nm. In a glove-box hosted vacuum deposition system at a pressure of 10$^{-7}$ torr (1 torr=133.322 Pa), 4,4'4"-tri(N-carbazolyl)triphenylamine (TCTA) was first deposited on top of PEDOT/PSS layer at deposition rate of 0.06 nm/s, yielding a 30 nm thick film. Then the deep blue emitter Compound 17 was deposited on top of TCTA to form a 30 nm thick film, followed by deposition of a 40 nm thick layer of 1,3,5-tris(N-phenylbenzimidizol-2-yl)benzene (TPBI), all at deposition rate around 0.06 nm/s. CsF and Al were then deposited successively at deposition rates of 0.005 and 0.2 nm/s, respectively. Each individual device has areas of 0.14 cm$^2$. Spectra is measured with an ocean optics HR4000 spectrometer and I-V light output measurements is taken with a Keithley 2400 SourceMeter and Newport 2832-C power meter and 818 UV detector. All device operation is carried out inside a nitrogen-filled glove-box.

Example 2.2

Another device (Device B) was constructed in accordance to Example 2.1, except that instead of neat Compound 17 layer being deposited on top of the TCTA, a mixture of Compound 17 (99.35%), tris(2-phenylpyridine anion) iridium (III) complex (Ir(ppy)3)(0.5%) and bis(2-phenyl quinolyl-N,C2')acetylacetonate iridium(III) (PQIr) (0.15%) was codeposited on top of TCTA to form a 15 nm thick film.

Example 2.3

Device C was fabricated as follows: the ITO coated glass substrates were cleaned by ultrasound in acetone, and consecutively in 2-propanol, baked at 110° C. for 3 hours, followed by treatment with oxygen plasma for 5 min. A layer of PEDOT: PSS (Baytron P purchased from H.C. Starck) was spin-coated at 3000 rpm onto the pre-cleaned and O$_2$-plasma treated (ITO)-substrate and annealed at 180° C. for 10 min, yielding a thickness of around 40 nm. In a glove-box hosted vacuum deposition system at a pressure of 10$^{-7}$ torr (1 torr=133.322 Pa), 4,4'-bis[N-(naphthyl)-N-phenyl-amino]biphenyl (α-NPD) was first deposited on top of PEDOT/PSS layer at deposition rate of 0.06 nm/s, yielding a 30 nm thick film. Then the deep blue emitter Compound 23 was deposited on top of α-NPD to form a 30 nm thick film, followed by deposition of a 40 nm thick layer of 1,3,5-tris(N-phenylbenzimidizol-2-yl)benzene (TPBI), all at deposition rate around 0.06 nm/s. CsF and Al were then deposited successively at deposition rates of 0.005 and 0.2 nm/s, respectively. Each individual device has areas of 0.14 cm$^2$. Spectra is measured with an ocean optics HR4000 spectrometer and I-V light output measurements is taken with a Keithley 2400 SourceMeter and Newport 2832-C power meter and 818 UV detector. All device operation is carried out inside a nitrogen-filled glove-box.

Example 2.4

Another device (Comparative Device A) was constructed in accordance to Example 2.3, except that instead of neat Compound 23 layer being deposited on top of the α-NPD, neat:

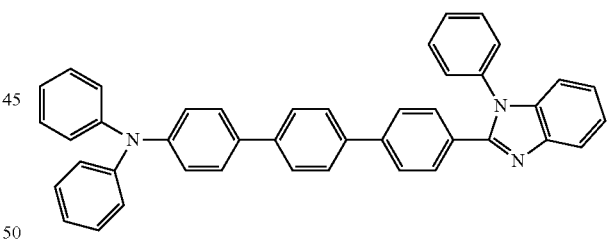

Comparative Compound A was deposited on top of α-NPD to form a 30 nm thick film.

Example 3

Device Performance

Example 3.1

Figure 1:
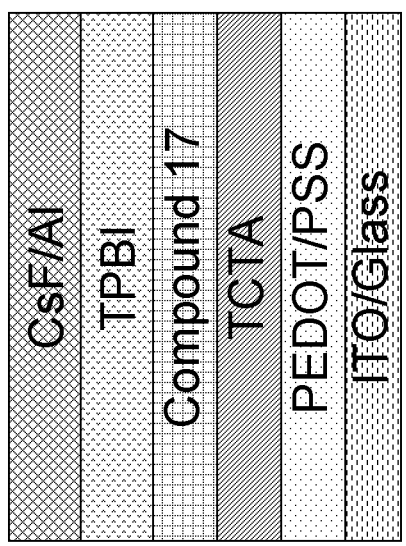
FIG. 1 shows an embodiment of an organic light-emitting device incorporating a compound of Formula 1.

Device A, a blue light emitting device, comprising Compound 21 and fabricated in accordance with Examples 1 and 2, was tested to determine the emissive qualities of the device by examining the (1) emissive intensity of Device A (intensity of the device [a.u.] as a function of wavelength; (2) determining the CIE coordinates of Device A; (3) determining the efficiency of Device A (current density and brightness as a function of the voltage applied to the device; and external quantum efficiency, power efficiency and brightness as a function of current density). All spectra were measured with an Ocean Optics HR 4000 spectrometer (Ocean Optics, Dunedin, Fla., USA) and I-V-L characteristics were taken with a Keithley 2400 SourceMeter (Keithley Instruments, Inc., Cleveland, Ohio, USA) and Newport 2832-C power meter and 818 UV detector (Newport, Corp., Irvine, Calif., USA). All device operation was performed inside a nitrogen-filled glove-box. An exemplary configuration of the device (Device A) is shown in FIG. 1 (Device structure: PEDOT:PSS/TCTA (30 nm)/Compound 17 (30 nm)/TPBi (40 nm)/CsF/Al). FIG. 2 shows electroluminescence spectrum of Device A, plus the CIE coordinate. The spectrum shows significant emission between 400 and 500 nm. The purity of the deep blue emitted radiation is demonstrated by the CIE coordinates (X=0.16; Y=0.05). In addition, as shown in FIGS. 3, 4 and 5, Device A demonstrates efficacy in conventional organic light emitting device parameters. Thus Compound 21 has demonstrated its effectiveness as a blue emitting compound in organic light emitting devices.

Example 3.2

Figure 7:
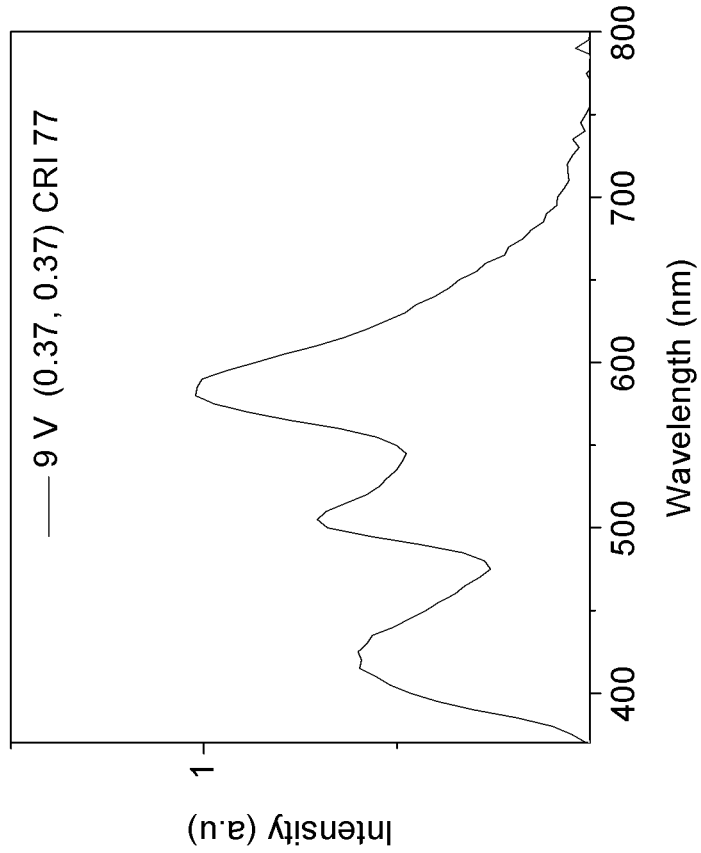
FIG. 7 is a graph depicting the electroluminescence spectrum and CIE coordinates of an embodiment of an organic light-emitting device of FIG. 6.
Figure 6:
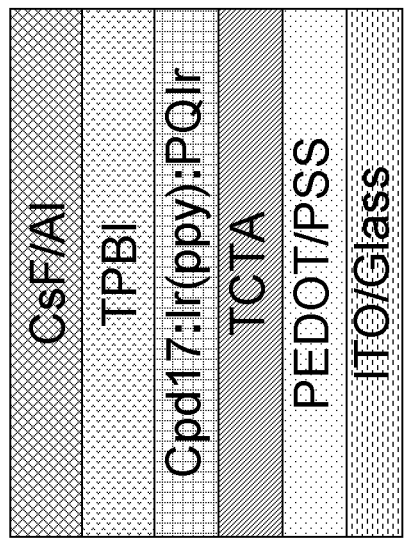
FIG. 6 shows an embodiment of a white light emitting organic light-emitting device incorporating a compound of Formula 1.

Device B, a white light emitting device, comprising Compound 17, tris(2-phenylpyridine)iridium (Ir(ppy)$_3$), and PQIr; and fabricated in accordance with Examples 1 and 2, was tested to determine the emissive qualities of the device by examining the (1) emissive intensity of Device B (intensity of the device [a.u.] as a function of wavelength; (2) determining the CIE coordinates of Device B; (3) determining the efficiency of Device B (current density and brightness as a function of the voltage applied to the device; and external quantum efficiency, power efficiency and brightness as a function of current density). All spectra were measured with an Ocean Optics HR 4000 spectrometer (Ocean Optics, Dunedin, Fla., USA) and I-V-L characteristics were taken with a Keithley 2400 SourceMeter (Keithley Instruments, Inc., Cleveland, Ohio, USA) and Newport 2832-C power meter and 818 UV detector (Newport, Corp., Irvine, Calif., USA). All device operation was performed inside a nitrogen-filled glove-box. An exemplary configuration of the device (Device B) is shown in FIG. 6 (Device structure: PEDOT:PSS/TCTA (30 nm)/Cmd 17:Ir(ppy)3 (0.5%):Ir(pq)2acac (PQIr) (0.15%) (15 nm)/TPBi (40 nm)/CsF/Al). FIG. 7 shows electroluminescence spectrum of Device B, plus the CIE coordinate and CRI value. The spectrum shows significant emission between 400 and 450; 500 and 525 and 575 and 625 nm. The purity of the white emitted radiation is demonstrated by the CIE coordinates (X=0.37; Y=0.37) and a color rendering index of 77. In addition, as shown in FIGS. 8, 9 and 10, Device B demonstrates efficacy in conventional organic light emitting device parameters. Thus Compound 17 has demonstrated its effectiveness as a blue emitting compound in white light emitting organic light emitting devices.

Example 3.3

Devices C and Comparative Device D, both blue light emitting devices, comprising Compound 23 and Comparative Compound A, respectively; and fabricated in accordance with Examples 2.3 and 2.4, were tested to determine the emissive qualities of the device by at least examining the (1) emissive intensity of Devices C and D (intensity of the device [a.u.] as a function of wavelength; (2) determining the efficiency of Devices C and D (current density and brightness as a function of the voltage applied to the device; and external quantum efficiency, power efficiency and brightness as a function of current density). All spectra were measured with an Ocean Optics HR 4000 spectrometer (Ocean Optics, Dunedin, Fla., USA) and I-V-L characteristics were taken with a Keithley 2400 SourceMeter (Keithley Instruments, Inc., Cleveland, Ohio, USA) and Newport 2832-C power meter and 818 UV detector (Newport, Corp., Irvine, Calif., USA). All device operation was performed inside a nitrogen-filled glove-box. An exemplary configuration of the devices (Devices C and D) are shown in FIG. 6 (Device C structure: PEDOT:PSS/α-NPD (30 nm)/Cmd 23 (30 nm)/TPBi (40 nm)/CsF/Al); Device D structure: PEDOT:PSS/α-NPD (30 nm)/ComparativeCmd A (30 nm)/TPBi (40 nm)/CsF/Al). The results are provided in Table 1.

TABLE 1

| | λem (nm) | V (V) | I (mA) | LE (cd/A) | PE (lm/W) | EQE | LT50 (h) |
|---|---|---|---|---|---|---|---|
| Comparative Cmd A | 457 | 3.73 | 1.55 | 5.16 | 4.34 | 3.68% | 8.3 |
| Compound 23 | 470 | 3.76 | 0.95 | 9.28 | 7.75 | 6.80% | 10 |

As shown in Table 1, Device C demonstrates almost twice the luminescent efficiency (9.28 cd/A [Device C], 5.16 cd/A [Device D]), almost twice the power efficiency (7.75 lm/W [Device C], 4.34 lm/W [Device D]), and almost twice the EQE (6.80% [Device C], 3.68% [Device D]), conventional organic light emitting device parameters. Thus Compound 23 has demonstrated its effectiveness as a blue emitting compound as compared to Comparative Example A in blue light emitting organic light emitting devices.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:
1. A compound represented by a formula:

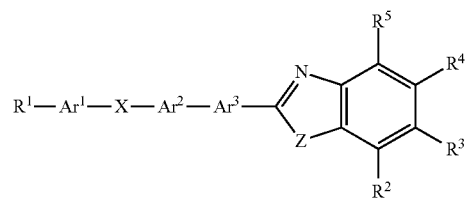

wherein $R^1$ is a $C_{1-10}O_{1-4}$ ether attaching at an oxygen atom or —$R^7$—$NR^8R^9$;
wherein $R^7$ is a single bond or optionally substituted $C_{6-10}$ aryloxy; and
$R^8$ and $R^9$ are independently optionally substituted $C_{6-10}$ aryl, wherein $R^8$ and $R^9$ optionally link together form a third ring comprising N;
$Ar^1$ is aryl having 0, 1, 2, 3, or 4 substituents independently selected from $C_{1-3}$ alkyl and F;
$Ar^2$ is p-interphenylene having 0, 1, 2, 3, or 4 substituents independently selected from $C_{1-3}$ alkyl and F;
X is O;
$Ar^3$ is p-interphenylene having 0, 1, 2, 3, or 4 substituents independently selected from $C_{1-3}$ alkyl and F; or $Ar^3$ is a single bond;

Z is NR⁶, wherein R⁶ is optionally substituted phenyl, optionally substituted —CH₂-phenyl, or optionally substituted (4-halophenyl)methyl; and R², R³, R⁴, and R⁵ are independently H, optionally substituted $C_{6-30}$ aryl, $C_{1-10}$ alkyl, or $C_{1-10}$ alkoxy.

2. The compound of claim 1, wherein R¹ is optionally substituted carbazolyl, optionally substituted carbazolylphenoxy, optionally substituted diphenyl amine, optionally substituted diphenylaminophenoxy, or $C_{1-10}$ alkoxy.

3. The compound of claim 2 wherein R¹ is methoxy,

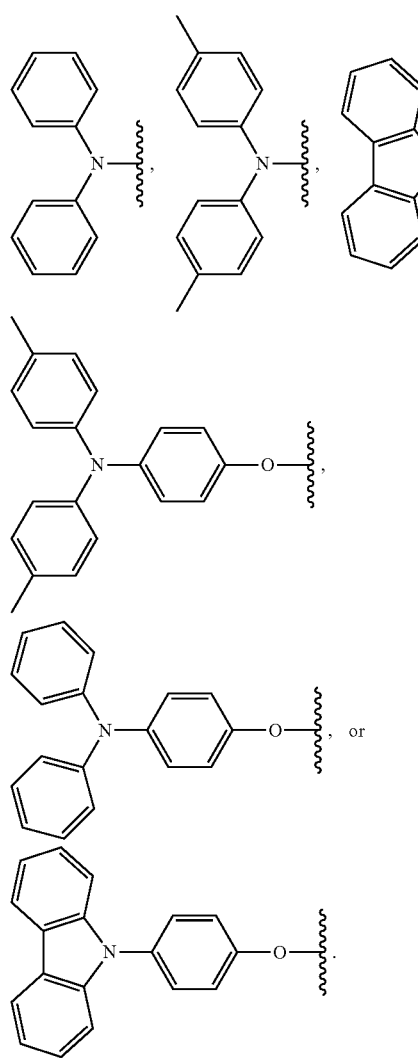

4. The compound of claim 1, wherein Ar¹ is optionally substituted p-interphenylene.

5. The compound of claim 1, wherein at least one of Ar¹, Ar², and Ar³ is unsubstituted p-interphenylene.

6. The compound of claim 1, wherein Z is NR⁶ and R⁶ is optionally substituted phenyl.

7. The compound of claim 6, wherein R¹ is selected from the group consisting of optionally substituted diphenyl amine, optionally substituted carbazolyl, optionally substituted p-carbazolylphenoxy, and optionally substituted p-diphenylaminophenoxy.

8. The compound of claim 1, wherein Ar³ is a single bond.

9. The compound of claim 8, wherein R¹ is optionally substituted diphenyl amine.

10. The compound of claim 8, wherein R¹ is optionally substituted carbazolyl.

11. The compound of claim 1, wherein Ar³ is p-interphenylene having 0, 1, 2, 3 or 4 substituents independently selected from $C_{1-3}$ alkyl and F.

12. The compound of claim 1, wherein the compound is selected from:

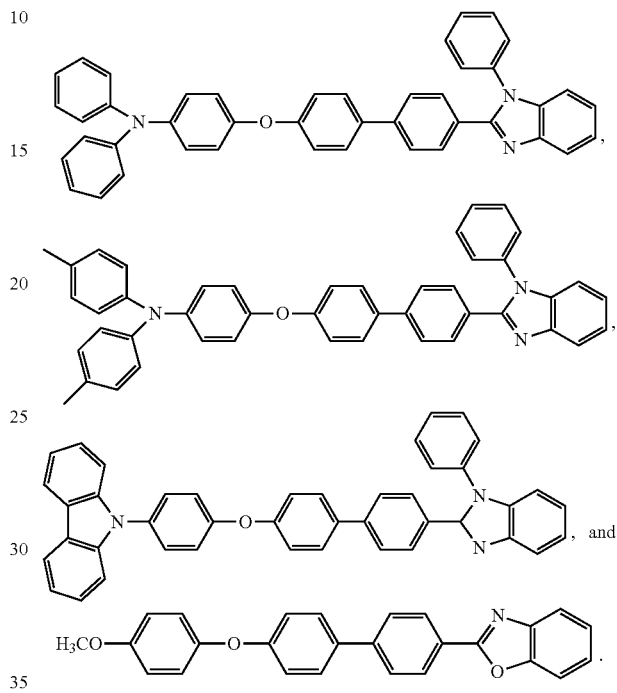

13. A compound represented by a formula:

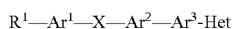

R¹—Ar¹—X—Ar²—Ar³-Het wherein R¹ is $C_{1-10}$ alkoxy, substituted carbazolyl, substituted diphenylamino, optionally substituted carbazolylphenoxy, or optionally substituted diphenylaminophenoxy;

Ar¹ is optionally substituted aryl;

Ar² is p-interphenylene having 0, 1, 2, 3, or 4 substituents independently selected from $C_{1-3}$ alkyl and F;

X is O;

Ar³ is p-interphenylene having 0, 1, 2, 3, or 4 substituents independently selected from $C_{1-3}$ alkyl and F; or Ar³ is a single bond; and Het is optionally substituted benzoimidazolyl.

14. A compound represented by a formula:

wherein R¹ is $C_{1-10}$ alkoxy, optionally substituted carbazolylphenoxy, or optionally substituted diphenylaminophenoxy; and Het is optionally substituted benzoimidazolyl.

15. The compound of claim 14, wherein the compound is selected from:

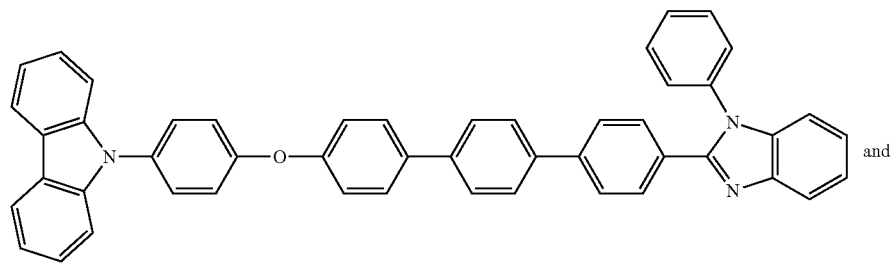

and

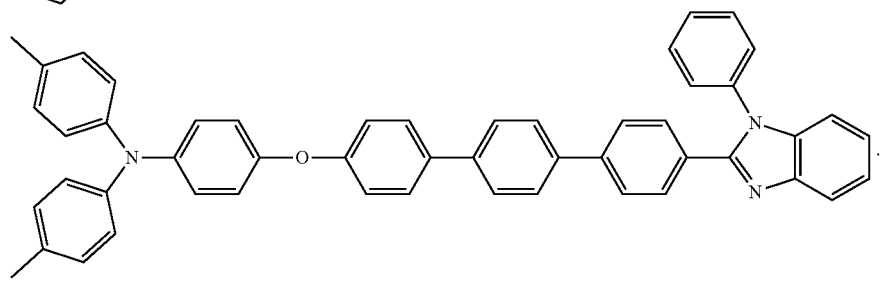

16. A light-emitting device, comprising:
a light-emitting layer comprising a compound according to claim 1.

17. A method of converting an electric potential difference to light comprising exposing a composition comprising a compound according to claim 1 to an electric potential difference to thereby produce light.

18. A method of converting light to an electric potential difference comprising exposing a composition comprising a compound according to claim 1 to light to thereby produce an electric potential difference.

* * * * *

UNITED STATES PATENT AND TRADEMARK OFFICE
CERTIFICATE OF CORRECTION

PATENT NO. : 8,927,121 B2  
APPLICATION NO. : 13/925625  
DATED : January 6, 2015  
INVENTOR(S) : Shijun Zheng et al.

Page 1 of 1

It is certified that error appears in the above-identified patent and that said Letters Patent is hereby corrected as shown below:

In the Specification

In column 59 at lines 3-12,

Change " 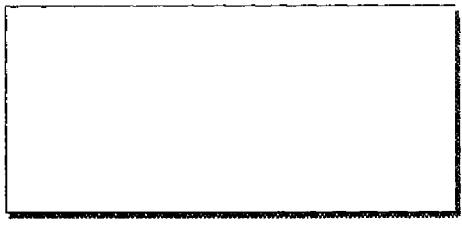 " to -- 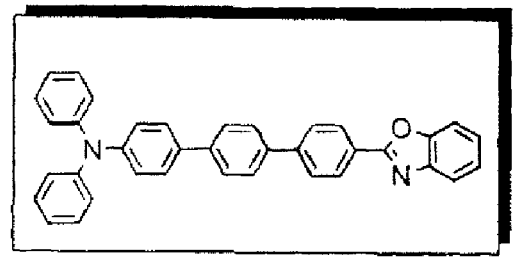 --.

Signed and Sealed this  
Eighth Day of September, 2015

Michelle K. Lee  
*Director of the United States Patent and Trademark Office*